(12) United States Patent
Banowski et al.

(10) Patent No.: US 9,549,883 B2
(45) Date of Patent: Jan. 24, 2017

(54) TEXTILE FRIENDLY NONAEROSOL-ANTIPERSPIRANTS WITH METHANSULFONIC

(71) Applicant: Henkel AG & Co. KGaA, Duesseldorf (DE)

(72) Inventors: Bernhard Banowski, Duesseldorf (DE); Marcus Claas, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 107 days.

(21) Appl. No.: 14/107,059

(22) Filed: Dec. 16, 2013

(65) Prior Publication Data
US 2014/0173833 A1    Jun. 26, 2014

(30) Foreign Application Priority Data
Dec. 21, 2012  (DE) .................. 10 2012 224 133

(51) Int. Cl.
*A61K 8/46* (2006.01)
*A61K 8/26* (2006.01)
*A61Q 15/00* (2006.01)

(52) U.S. Cl.
CPC ............. *A61K 8/466* (2013.01); *A61K 8/26* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 1,014,599 A | 1/1912 | Kitselman | |
| 2,571,030 A | 10/1951 | Govett et al. | |
| 3,887,692 A | 6/1975 | Gilman | |
| 3,904,741 A | 9/1975 | Jones et al. | |
| 3,974,270 A | 8/1976 | Kenkare et al. | |
| 4,110,428 A | 8/1978 | Kuhn et al. | |
| 4,359,456 A | 11/1982 | Gosling et al. | |
| 4,511,554 A | 4/1985 | Geria et al. | |
| 4,775,528 A | 10/1988 | Callaghan et al. | |
| 5,643,558 A | 7/1997 | Provancal et al. | |
| 5,643,559 A | 7/1997 | Eigen et al. | |
| 5,676,937 A | 10/1997 | Eigen et al. | |
| 5,925,338 A | 7/1999 | Karassik et al. | |
| 6,010,688 A | 1/2000 | Shen | |
| 6,042,816 A | 3/2000 | Shen | |
| 6,074,632 A | 6/2000 | Shen | |
| 6,245,325 B1 | 6/2001 | Shen | |
| 6,436,381 B1 | 8/2002 | Carrillo et al. | |
| 6,649,152 B2 | 11/2003 | Carrillo et al. | |
| 6,663,854 B1 | 12/2003 | Shen et al. | |
| 6,923,952 B2 | 8/2005 | Allen et al. | |
| 7,105,691 B2 | 9/2006 | Holerca et al. | |
| 7,294,330 B2 | 11/2007 | Banowski et al. | |
| 2004/0009133 A1 | 1/2004 | Kolodzik et al. | |
| 2005/0203179 A1 | 9/2005 | Banowski et al. | |
| 2011/0190229 A1* | 8/2011 | Orlow et al. | ............ 514/27 |
| 2012/0058064 A1 | 3/2012 | Urban et al. | |

FOREIGN PATENT DOCUMENTS

| | | |
|---|---|---|
| DE | 3018132 A1 | 11/1981 |
| DE | 102010000746 A1 | 1/2011 |
| EP | 1428519 A2 | 6/2004 |
| EP | 1428520 A2 | 6/2004 |
| EP | 1430879 A2 | 6/2004 |
| GB | 1347950 | 2/1974 |
| GB | 2048229 A | 12/1980 |
| GB | 2335596 A | 9/1999 |
| WO | 91/05541 A1 | 5/1991 |
| WO | 98/18441 A1 | 5/1998 |
| WO | 01/99376 A2 | 12/2001 |
| WO | 2006/079934 A2 | 8/2006 |
| WO | 2010/031657 A2 | 3/2010 |
| WO | 2010/046291 A2 | 4/2010 |
| WO | 2011/050044 A1 | 4/2011 |

OTHER PUBLICATIONS

Kirk-Othmer, "Encyclopedia of Chemical Technology", Third Edition, vol. 8, pp. 913-916, 1979.
PCT International Search Report (PCT/EP2013/076656) dated December 8, 2014.
Tully, "Sulfonic Acids", Kirk-Othmer Encyclopedia of Chemical Technology, Dec. 4, 2000, XP055134265.

* cited by examiner

*Primary Examiner* — Necholus Ogden, Jr.
(74) *Attorney, Agent, or Firm* — P. Scott Smith

(57) ABSTRACT

Cosmetic antiperspirants for nonaerosol use, having a content of methanesulfonic acid and/or at least one physiologically acceptable salt of methanesulfonic acid, which exhibit less textile staining than known antiperspirants.

12 Claims, No Drawings

TEXTILE FRIENDLY NONAEROSOL-ANTIPERSPIRANTS WITH METHANSULFONIC

FIELD OF THE INVENTION

The present invention generally relates to cosmetic antiperspirants that exhibit less textile staining than known antiperspirants.

BACKGROUND OF THE INVENTION

Washing, cleaning, and caring for one's own body are basic human needs, and modern industry is continually attempting to meet these human needs in many ways. Long-lasting elimination of, or at least reduction in, body odor is particularly important for daily hygiene. Numerous special deodorizing or perspiration-inhibiting toiletries, which have been developed for use in body regions having a high density of sweat glands, in particular in the axillary region, are known in the existing art. These are formulated in a very wide variety of administration forms, for example as powders, in stick form, as an aerosol spray, pump spray, liquid and gelled roll-on application, cream, gel, and as an impregnated flexible substrate (deodorant pads).

Cosmetic antiperspirants include in any case at least one perspiration-inhibiting salt. Usually at least one oil or one fatty substance is also included, and in any case always a fragrance component i.e. a perfume.

When used regularly, antiperspirants can result in clearly visible colored textile stains. These are often yellow spots that cannot be removed even with intensive washing. Stain formation is based on a complex interaction of formulation constituents, perspiration, and the washing agent being used. It is probable that firstly, insoluble aluminum compounds form on and within the fibers. The yellow color as a rule occurs with a time delay, and is brought about at least in part by the oxidation of unsaturated fatty acids that are present as insoluble aluminum salts. Unfortunately, various factors can interact unexpectedly here, and pronounced yellow stains can form on textiles depending on the selection of the perfume oil and the washing agent, and depending on individual perspiration quantity and composition.

Insoluble compounds form as a result of the interaction of washing agents and antiperspirant active substances, and can absorb onto a textile. These insoluble compounds form white, hard residua that usually become apparent on the textile only after several cycles of staining and washing. These white residua are not soluble in water, and also cannot be removed using a standard washing method. They are particularly apparent on light- or dark-colored textiles. Skillful selection of additives results in an appreciably reduced formation, or delayed formation, of these insoluble deposits.

Cosmetic oils or polyols are used in order to mask white residua on dark textiles, for example as a result of transfer of the products from the skin onto a textile when it is put on. These masking agents can likewise be absorbed onto a textile. Depending on the chemical composition, these masking agents can be removed only partly or not at all using a standard washing process. The hydrophobic masking agent builds up on the textile and results in a dark, greasy/oily stain that, among other effects, can also modify the haptics of the textiles in the stained region. Skillful choice of additives results in an appreciably reduced formation, or delayed formation, of these oily/greasy dark stains.

A demand therefore exists for antiperspirant formulations that can reliably prevent the formation of yellow, white, and/or greasy spots.

A variety of ingredients are added in the existing art in order to protect textiles from such permanent stains. Surfactants are an additive that is often used, as disclosed e.g. in WO 2010/097205 A2. Selection of the oil components can also decrease or even increase textile staining (see e.g. U.S. Pat. Nos. 5,925,338, 4,511,554, or No. 3,974,270).

It is therefore desirable to furnish cosmetic antiperspirants that include a perspiration-inhibiting aluminum salt and do not result, or result only to a greatly reduced extent, in persistent textile discoloration.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A perspiration-inhibiting cosmetic agent for nonaerosol utilization, including in a cosmetically acceptable carrier a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the agent; and in addition thereto b) methanesulfonic acid of the following formula (MS-1)

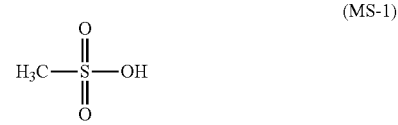

or at least one physiologically acceptable salt of methanesulfonic acid.

Use of methanesulfonic acid of formula (MS-1)

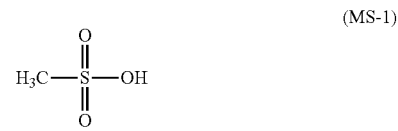

and/or at least one physiologically acceptable salt of methanesulfonic acid in a cosmetically acceptable carrier, including at least one perspiration-inhibiting aluminum salt that is preferably zirconium-free, in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the composition, to reduce or prevent textile discolorations and/or textile stains, where the "wt %" indications refer in each case to the total weight of the agent.

A method for preventing and/or reducing textile discolorations and/or textile spots, where the method comprises the following method steps: a) producing a perspiration-inhibiting cosmetic agent by mixing at least one perspiration-inhibiting aluminum salt, which is preferably zirconium-free, in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the agent, with a cosmetically acceptable carrier and with at least one methanesulfonic acid of the following formula (MS-1),

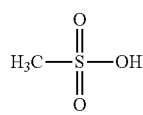

(MS-1)

or at least one physiologically acceptable salt of methanesulfonic acid; e) applying the perspiration-inhibiting cosmetic agent onto the skin, in particular onto the skin of the armpits; f) wearing a textile garment over the treated skin; and g) washing the textile garment, in particular repeatedly washing the textile garment, where no, or reduced, textile discolorations and/or textile spots occur after washing, in particular after repeated washing.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that an addition of methanesulfonic acid and/or at least one physiologically acceptable salt of methanesulfonic acid achieves the stated objects very effectively, and is outstandingly suitable as a discoloration inhibitor for use in cosmetic antiperspirants.

A first subject of the present Application is therefore a perspiration-inhibiting cosmetic agent for nonaerosol utilization, including in a cosmetically acceptable carrier a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the agent, and in addition thereto b) methanesulfonic acid of the following formula (MS-1)

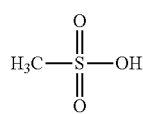

(MS-1)

and/or at least one physiologically acceptable salt of methanesulfonic acid.

A further subject of the present Application is the use of methanesulfonic acid of the following formula (MS-1)

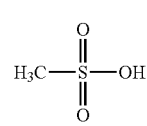

(MS-1)

and/or at least one physiologically acceptable salt of methanesulfonic acid, in a perspiration-inhibiting cosmetic agent including, in a cosmetically acceptable carrier, at least one perspiration-inhibiting aluminum salt that is preferably zirconium-free, in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the composition, to reduce or prevent textile discolorations and/or textile stains, where the "wt %" indications refer in each case to the total weight of the agent.

The statements made below concerning the agents according to the present invention apply mutatis mutandis with regard to preferred embodiments of the use according to the present invention.

Preferred agents according to the present invention are characterized in that the physiologically acceptable salts of methanesulfonic acid are selected from sodium, potassium, magnesium, calcium, manganese, zinc, and aluminum salts of methanesulfonic acid. Methanesulfonic acid itself is extraordinarily preferred.

Further preferred agents according to the present invention are characterized in that methanesulfonic acid and/or at least one physiologically acceptable salt thereof is included in a total quantity from 0.05 to 5 wt %, preferably 0.1 to 3 wt %, particularly preferably 0.5 to 2.5 wt %, extraordinarily preferably 1 to 2 wt %, based in each case on the total weight of the agent.

Be it noted at this juncture that unless otherwise indicated, the "wt %" indication refers in each case to the total weight of the agent according to the present invention.

The terms "agent according to the present invention" and "composition according to the present invention" are used synonymously in the present Application.

"Standard conditions" for purposes of the present Application are a temperature of 20° C. and a pressure of 1013 mbar. Indications of melting point likewise refer to a pressure of 1013 mbar.

The agents according to the present invention include a cosmetically acceptable carrier. Preferably according to the present invention, the cosmetically acceptable carrier is liquid or solid under standard conditions (20° C., 1013 mbar). Further cosmetically acceptable carriers preferred according to the present invention encompass at least one cosmetic oil that is not a fragrance and not an essential oil.

The cosmetic oils that are liquid under standard conditions are not miscible with water.

When a "cosmetic oil" is discussed in the present Application, this always refers to a cosmetic oil that is not a fragrance and not an essential oil, is liquid under standard conditions, and is not miscible with water.

In a first preferred embodiment of the invention, the agent according to the present invention includes zero to a maximum of 10 wt % free water, preferably zero to a maximum of 5 wt % free water. The concentration of water of crystallization, water of hydration, or similarly molecularly bound water that is included in the constituents used, in particular in the perspiration-inhibiting active substances, does not represent free water for purposes of the present Application and is therefore not taken into account when calculating the quantity of water.

It has been found, surprisingly, that the textile discoloration-reducing or -preventing effect of the methanesulfonic acid emerges particularly well in agents that include 15 to 96 wt % free water.

In particularly preferred embodiment of the invention, the agent according to the present invention therefore includes free water in a total quantity from 15 to 96 wt %, preferably 25 to 80 wt %, particularly preferably 30 to 70 wt %, extraordinarily preferably 40 to 60 wt %, based in each case on the total weight of the agent according to the present invention.

Antiperspirant Active Substances

The compositions according to the present invention include as an antiperspirant active substance at least one perspiration-inhibiting aluminum salt in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the composition.

It can be preferred according to the present invention for the cosmetic agent to be free of zirconium compounds.

The perspiration-inhibiting aluminum salts are preferably selected from water-soluble astringent inorganic and organic salts of aluminum and of aluminum-zirconium mixtures. Aluminosilicates and zeolites are not included according to the present invention among the antiperspirant active substances. "Water solubility" is understood according to the present invention as a solubility of at least 3 wt % at 20° C., i.e. that quantities of at least 3 g of the antiperspirant active substance are soluble in 97 g water at 20° C.

Particularly preferred antiperspirant active substances are selected from aluminum chlorohydrate, in particular aluminum chlorohydrate having the general formula $[Al_2(OH)_5Cl.1-6H_2O]_n$, preferably $[Al_2(OH)_5Cl.2-3H_2O]_n$, which can be present in nonactivated or activated (depolymerized) form, as well as aluminum chlorohydrate having the general formula $[Al_2(OH)_4Cl_2.1-6H_2O]_n$, preferably $[Al_2(OH)_4Cl_2.2-3H_2O]_n$, which can be present in nonactivated or activated (depolymerized) form.

The manufacture of preferred antiperspirant active substances is disclosed, for example, in U.S. Pat. Nos. 3,887,692, 3,904,741, 4,359,456, GB 2048229, and GB 1347950.

Also preferred are aluminum sesquichlorohydrate, aluminum dichlorohydrate, aluminum chlorohydrex propylene glycol (PG) or aluminum chlorohydrex polyethylene glycol (PEG), aluminum or aluminum zirconium glycol complexes, e.g. aluminum or aluminum zirconium propylene glycol complexes, aluminum sesquichlorohydrex PG or aluminum sesquichlorohydrex PEG, aluminum PG dichlorohydrex or aluminum PEG dichlorohydrex, aluminum hydroxide, furthermore selected from aluminum zirconium chlorohydrates, such as aluminum zirconium trichlorohydrate, aluminum zirconium tetrachlorohydrate, aluminum zirconium pentachlorohydrate, aluminum zirconium octachlorohydrate, aluminum zirconium chlorohydrate/glycine complexes, such as aluminum zirconium trichlorohydrex glycine, aluminum zirconium tetrachlorohydrex glycine, aluminum zirconium pentachlorohydrex glycine, aluminum zirconium octachlorohydrex glycine, potassium aluminum sulfate ($KAl(SO_4)_2.12H_2O$, alum), aluminum undecylenoyl collagen amino acid, sodium aluminum lactate+aluminum sulfate, sodium aluminum chlorohydroxylactate, aluminum bromohydrate, aluminum chloride, aluminum salts of lipoamino acids, aluminum sulfate, aluminum lactate, aluminum chlorohydroxyallantoinate, and sodium aluminum chlorohydroxylactate.

Antiperspirant active substances particularly preferred according to the present invention are selected from so-called "activated" aluminum and aluminum-zirconium salts, which are also referred to as "enhanced activity" antiperspirant active substances. Such active substances are known in the existing art and also commercially obtainable. Their manufacture is disclosed, for example, in GB 2048229, U.S. Pat. Nos. 4,775,528, and U.S. Pat. No. 6,010,688. Activated aluminum and aluminum-zirconium salts are generally produced by heat treatment of a relatively dilute solution of the salt (e.g. approximately 10 wt % salt), in order to increase its HPLC peak 4 to peak 3 area ratio. The activated salt can then be dried, in particular spray-dried, to a powder. Besides spray drying, drum drying is, for example, also suitable.

Activated aluminum and aluminum-zirconium salts typically have an HPLC peak 4 to peak 3 area ratio of at least 0.4, preferably at least 0.7, particularly preferably at 0.9, where at least 70% of the aluminum is to be associated with these peaks.

Activated aluminum and aluminum-zirconium salts do not necessarily need to be used as a spray-dried powder. Perspiration-inhibiting active substances that are likewise preferred according to the present invention are nonaqueous solutions or solubilizates of an activated perspiration-inhibiting aluminum or aluminum-zirconium salt, for example in accordance with U.S. Pat. No. 6,010,688, which are stabilized against loss of activation (rapid decrease in the HPLC peak 4 to peak 3 area ratio) of the salt by the addition of an effective quantity of a polyvalent alcohol that comprises 3 to 6 carbon atoms and 3 to 6 hydroxyl groups, preferably propylene glycol, sorbitol, and pentaerythritol. Preferred compositions are, for example, those that include, in wt % (USP): 18 to 45 wt % of an activated aluminum or aluminum-zirconium salt, 55 to 82 wt % of at least one anhydrous polyvalent alcohol having 3 to 6 carbon atoms and 3 to 6 hydroxyl groups, preferably 1,2-propylene glycol, 1,3-butylene glycol, diethylene glycol, dipropylene glycol, glycerol, sorbitol, and pentaerythritol, particularly preferably 1,2-propylene glycol.

Also particularly preferred are complexes of activated perspiration-inhibiting aluminum or aluminum-zirconium salts with a polyvalent alcohol which include 20 to 50 wt %, particularly preferably 20 to 42 wt %, activated perspiration-inhibiting aluminum or aluminum-zirconium salt and 2 to 16 wt % molecularly bound water, the remainder (to 100 wt %) being at least one polyvalent alcohol having 3 to 6 carbon atoms and 3 to 6 hydroxyl groups. Propylene glycol, propylene glycol/sorbitol mixtures, and propylene glycol/pentaerythritol mixtures are preferred alcohols of this kind. Complexes of this kind, preferred according to the present invention, of an activated perspiration-inhibiting aluminum or aluminum-zirconium salt with a polyvalent alcohol are disclosed e.g. in U.S. Pat. No. 5,643,558 and U.S. Pat. No. 6,245,325.

Further preferred perspiration-inhibiting active substances are basic calcium-aluminum salts such as those disclosed e.g. in U.S. Pat. No. 2,571,030. These salts are manufactured by reacting calcium carbonate with aluminum chlorhydroxide or aluminum chloride and aluminum powder, or by adding calcium chloride dihydrate to aluminum chlorhydroxide.

Further preferred perspiration-inhibiting active substances are aluminum-zirconium complexes such as those disclosed e.g. in U.S. Pat. No. 4,017,599, which are buffered with salts of amino acids, in particular with alkali and alkaline-earth glycinates.

Further preferred perspiration-inhibiting active substances are activated aluminum or aluminum-zirconium salts such as those disclosed e.g. in U.S. Pat. No. 6,245,325 or U.S. Pat. No. 6,042,816, including 5 to 78 wt % (USP) of an activated perspiration-inhibiting aluminum or aluminum-zirconium salt, an amino acid or hydroxyalkane acid in a quantity such as to furnish a weight ratio of (amino acid or hydroxyalkane acid) to (Al+Zr) from 2:1 to 1:20, and preferably 1:1 to 1:10, as well as a water-soluble calcium salt in a quantity such as to furnish a Ca:(Al+Zr) weight ratio from 1:1 to 1:28, and preferably 1:2 to 1:25.

Particularly preferred solid activated perspiration-inhibiting salt compositions, for example according to U.S. Pat. No. 6,245,325 or U.S. Pat. No. 6,042,816, include 48 to 78 wt % (USP), preferably 66 to 75 wt % of an activated aluminum or aluminum-zirconium salt, and 1 to 16 wt %, preferably 4 to 13 wt % molecularly bound water (water of hydration), furthermore a water-soluble calcium salt in a sufficient quantity that the Ca:(Al+Zr) weight ratio is 1:1 to 1:28, preferably 1:2 to 1:25, and sufficient amino acid that the (amino acid) to (Al+Zr) weight ratio is 2:1 to 1:20, preferably 1:1 to 1:10.

Further particularly preferred solid perspiration-inhibiting activated salt compositions, for example according to U.S. Pat. No. 6,245,325 or U.S. Pat. No. 6,042,816, include 48 to 78 wt % (USP), preferably 66 to 75 wt %, of an activated aluminum or aluminum-zirconium salt, and 1 to 16 wt %, preferably 4 to 13 wt % molecularly bound water (water of hydration), furthermore water-soluble calcium salt in a quantity sufficient that the Ca:(Al+Zr) weight ratio is 1:1 to 1:28, preferably 1:2 to 1:25, and sufficient glycine that the glycine to (Al+Zr) weight ratio is 2:1 to 1:20, preferably 1:1 to 1:10.

Further particularly preferred solid perspiration-inhibiting activated salt compositions, for example according to U.S. Pat. No. 6,245,325 or U.S. Pat. No. 6,042,816, include 48 to 78 wt % (USP), preferably 66 to 75 wt %, of an activated aluminum or aluminum-zirconium salt, and 1 to 16 wt %, preferably 4 to 13 wt % molecularly bound water, furthermore water-soluble calcium salt in a quantity sufficient that the Ca:(Al+Zr) weight ratio is 1:1 to 1:28, preferably 1:2 to 1:25, and sufficient hydroxyalkane acid that the (hydroxyalkane acid) to (Al+Zr) weight ratio is 2:1 to 1:20, preferably 1:1 to 1:10.

Amino acids preferred for stabilization of the perspiration-inhibiting salts are selected from glycine, alanine, leucine, isoleucine, β-alanine, valine, cysteine, serine, tryptophan, phenylalanine, methionine, β-amino-n-butanoic acid, and γ-amino-n-butanoic acid and salts thereof, in each case in the d-form, the l-form, and the dl-form; glycine is particularly preferred.

Hydroxyalkane acids preferred for stabilization of the perspiration-inhibiting salts are selected from glycolic acid and lactic acid.

Further preferred activated aluminum salts are those of the general formula $Al_2(OH)_{6-a}Xa$, in which X is Cl, Br, I, or $NO_3$ and "a" is a value from 0.3 to 5, preferably from 0.8 to 2.5, and particularly preferably 1 to 2, so that the molar ratio Al:X is 0.9:1 to 2.1:1, as disclosed e.g. in U.S. Pat. No. 6,074,632. Some water of hydration is generally associatively bound into these salts, typically 1 to 6 mol water per mol salt. Aluminum chlorohydrate is particularly preferred (i.e. X is Cl in the formula above), and especially 5/6-basic aluminum chlorohydrate in which "a" is equal to 1, so that the molar ratio of aluminum to chlorine is 1.9:1 to 2.1:1.

Preferred activated aluminum-zirconium salts are those that represent mixtures or complexes of the above-described aluminum salts with zirconium salts of the formula $ZrO(OH)_{2-pb}Y_b$, where Y is Br, I, $NO_3$, or $SO_4$, b is a rational number from 0.8 to 2, and p is the valency of Y, as disclosed e.g. in U.S. Pat. No. 6,074,632. The zirconium salts as a rule likewise have some associatively bound water of hydration, typically 1 to 7 mol water per mol salt. The zirconium salt is by preference zirconyl hydroxychloride having the formula $ZrO(OH)_{2-b}Cl_b$, in which b is a rational number from 0.8 to 2, preferably 1.0 to 1.9. Preferred aluminum-zirconium salts have an Al:Zr molar ratio from 2 to 10, and a metal:(X+Y) ratio from 0.73 to 2.1, preferably 0.9 to 1.5. A particularly preferred salt is aluminum-zirconium chlorohydrate (i.e. X and Y are Cl), which has an Al:Zr ratio from 2 to 10 and a molar metal:Cl ratio from 0.9 to 2.1. The term "aluminum-zirconium chlorohydrate" encompasses the tri-, tetra-, penta- and octachlorohydrate forms. Further preferred perspiration-inhibiting active substances are disclosed in U.S. Pat. No. 6,663,854 and US 2004 0009133.

Preferred perspiration-inhibiting aluminum-zirconium salts have a molar metal-to-chloride ratio from 0.9 to 1.5, preferably 0.9 to 1.3, particularly preferably 0.9 to 1.1.

Zirconium-free aluminum salts particularly preferred according to the present invention have a molar metal-to-chloride ratio from 1.9 to 2.1. Zirconium-free aluminum sesquichlorohydrates particularly preferred according to the present invention have a molar metal-to-chloride ratio from 1.5:1 to 1.8:1.

Preferred aluminum zirconium chlorohydrates generally have the empirical formula $Al_nZr(OH)_{[3n+4-m(n+1)]}(Cl)_{[m(n+1)]}$, where n=2.0 to 10.0, preferably 3.0 to 8.0, m=0.77 to 1.11 (corresponding to a molar ratio of metal (Al+Zr) to chloride from 1.3 to 0.9), preferably m=0.91 to 1.11 (corresponding to M:Cl=1.1 to 0.9), and particularly preferably m=1.00 to 1.11 (corresponding to M:Cl=1.0 to 0.9), also very preferably m=1.02 to 1.11 (corresponding to M:Cl=0.98 to 0.9) and very preferably m=1.04 to 1.11 (corresponding to M:Cl=0.96 to 0.9). Some water of hydration is generally associatively bound in these salts, typically 1 to 6 mol water per mol salt, corresponding 1 to 16 wt %, preferably 4 to 13 wt % water of hydration.

Preferred aluminum zirconium chlorohydrates are usually associated with an amino acid in order to prevent polymerization of the zirconium species during manufacture. Preferred stabilizing amino acids are selected from glycine, alanine, leucine, isoleucine, β-alanine, cysteine, valine, serine, tryptophan, phenylalanine, methionine, β-amino-n-butanoic acid, and γ-amino-n-butanoic acid, and salts thereof, respectively in the d-form, l-form, and dl-form; glycine is particularly preferred. The amino acid is included in the salt in a quantity from 1 to 3 mol, preferably 1.3 to 1.8 mol, in each case per mol of zirconium.

Preferred perspiration-inhibiting salts are aluminum zirconium tetrachlorohydrates (Al:Zr=2 to 6; M:Cl=0.9 to 1.3), in particular salts having a molar metal-to-chloride ratio from 0.9 to 1.1, preferably 0.9 to 1.0.

Also preferred according to the present invention are aluminum zirconium chlorohydrate glycine salts that are stabilized with betaine $((CH_3)_3N^+—CH_2—COO^-)$. Particularly preferred corresponding compounds have a molar ratio of total (betaine+glycine) to Zr from (0.1 to 3.0):1, preferably (0.7 to 1.5):1, and a molar ratio of betaine to glycine of at least 0.001:1. Corresponding compounds are disclosed, for example, in U.S. Pat. No. 7,105,691.

In a particularly preferred embodiment according to the present invention a so-called "activated" salt is included as a particularly effective antiperspirant salt, in particular one having a high HPLC peak 5 aluminum content, in particular having a peak 5 area of at least 33%, particularly preferably at least 45%, based on the total area under peaks 2 to 5, measured by HPLC in a 10 wt % aqueous solution of the active substance under conditions in which the aluminum species are resolved into at least four successive peaks (referred to as peaks 2 to 5). Preferred aluminum-zirconium salts having a high HPLC peak 5 aluminum content (also called "$E^5AZCH$") are disclosed, for example, in U.S. Pat. No. 6,436,381 and U.S. Pat. No. 6,649,152.

Also preferred are those activated "$E^5AZCH$" salts whose HPLC peak-4 to peak-3 area ratio is equal to at least 0.4, preferably at least 0.7, particularly preferably at least 0.9. Further particularly preferred antiperspirant active substances are those aluminum-zirconium salts having a high HPLC peak 5 aluminum content that are additionally stabilized with a water-soluble strontium salt and/or with a water-soluble calcium salt. Corresponding salts are disclosed, for example, in U.S. Pat. No. 6,923,952.

Formulation of the agents according to the present invention in a specific administration form, for example an antiperspirant roll-on or an antiperspirant stick, antiperspirant gel, is preferably based on the requirements of the intended use.

Agents according to the present invention can be present in solid, semi-solid, liquid, dispersed, emulsified, suspended, or gelled form.

In a particularly preferred embodiment, the agents according to the present invention are present in liquid form or in viscous flowable form. Application can occur preferably using a roll-on ball applicator. Such rollers comprise a ball, mounted in a ball socket, that can be moved by motion over a surface. In that context the ball picks up some of the agent to be distributed and delivers it to the surface to be treated. The package for the agents according to the present invention can be opaque, but can also be transparent or translucent.

The term "liquid" also encompasses for purposes of the invention any dispersion of solids in liquids. Agents according to the present invention can also be present as pastes, salves, lotions, or creams. Solid agents can be present, for example, as a stick.

Application can also occur using substrates that are acted upon by an agent according to the present invention. Moist cloths, i.e. moist cloths prefabricated for the user and preferably packaged individually, such as those well known e.g. from the glass cleaning sector or from the sector of moist toilet papers, are particularly preferred. Such moist cloths, which can advantageously also include preservatives, are then impregnated or acted upon by an agent according to the present invention; preferably, they are individually packaged. They can be used, for example, as a deodorant cloth, which is of particular interest for use while traveling.

Preferred substrate materials are preferably selected from porous flat cloths. They can be made of a fibrous or cellular flexible material that exhibits sufficient mechanical stability simultaneously with softness for use on the skin. Included among these cloths are cloths made of woven and nonwoven synthetic and natural fibers, felt, paper, or foam, for example hydrophilic polyurethane foam.

Conventional cloths made of nonwoven material (nonwoven fabrics) are preferably used here. Nonwoven fabrics are defined in general as adhesively bonded fibrous products that comprise a mat or a layered fiber structure, or those that encompass fiber mats in which the fibers are distributed randomly or in a statistical arrangement. The fibers can be natural, such as wool, silk, jute, hemp, cotton, linen, sisal, or ramie; or synthetic, such as rayon, cellulose esters, cellulose, polyvinyl derivatives, polyolefins, polyamides, or polyesters. In general, any fiber diameter or titer is suitable for the present invention. Because of the random or statistical arrangement of fibers in the nonwoven material, which impart excellent strength in all directions, the nonwoven materials used here have no tendency to tear or disintegrate. Examples of nonwoven materials that are suitable as substrates in the present invention are known, for example, from WO 98/18441. Preferred porous and planar cleaning cloths are made of one or several fiber materials, in particular of cotton, finished cotton, polyamide, polyester, or mixtures thereof. The substrates in cloth form preferably have an area from 10 to 400 $cm^2$, preferably from 50 to 300 $cm^2$, particularly preferably from 100 to 200 $cm^2$. The gram weight of the cloth material is usually between 20 and 1000 $g/m^2$, preferably 30 and 500 $g/m^2$, and in particular 50 to 150 $g/m^2$. Deodorizing or perspiration-inhibiting substrates preferred according to the present invention can be obtained by immersion or impregnation, or also by melting an agent according to the present invention onto a substrate.

The agents according to the present invention, preferably liquid agents, can also be multi-phase; the phases can, for example, be arranged horizontally, i.e. one above another, or vertically, i.e. next to one another. The system can also be dispersed, in which e.g. the solid constituents are distributed inhomogeneously in the liquid matrix, so that a dispersed system of this kind should be shaken before use.

In a preferred embodiment the agents according to the present invention are present as a water-in-oil emulsion that includes methanesulfonic acid and/or at least one physiologically acceptable salt thereof. In another preferred embodiment the agents according to the present invention are present as an oil-in-water emulsion that includes methanesulfonic acid and/or at least one physiologically acceptable salt thereof, preferably in a total quantity from 0.05 to 5 wt %, preferably 0.1 to 3 wt %, particularly preferably 0.5 to 2.5 wt %, extraordinarily preferably 1 to 2 wt %, based in each case on the total weight of the agent.

In a further preferred embodiment the agents according to the present invention are characterized in that they are an antiperspirant-water-in-oil emulsion that includes methanesulfonic acid and/or at least one physiologically acceptable salt thereof, preferably in a total quantity from 0.05 to 5 wt %, preferably 0.1 to 3 wt %, particularly preferably 0.5 to 2.5 wt %, extraordinarily preferably 1 to 2 wt %, furthermore 15 to 90 wt %, preferably 25 to 70 wt %, particularly preferably 30 to 50 wt %, extraordinarily preferably 35 to 45 wt % water, at least one emulsifier agent, as well as at least one cosmetic fat or oil, the "wt %" indications referring in each case to the total weight of the agent according to the present invention.

In a further preferred embodiment the agents according to the present invention are characterized in that they are an antiperspirant-oil-in-water emulsion that includes methanesulfonic acid and/or at least one physiologically acceptable salt thereof, preferably in a total quantity from 0.05 to 5 wt %, preferably 0.1 to 3 wt %, particularly preferably 0.5 to 2.5 wt %, extraordinarily preferably 1 to 2 wt %, furthermore 15 to 90 wt %, preferably 25 to 70 wt %, particularly preferably 30 to 50 wt %, extraordinarily preferably 35 to 45 wt % water, at least one emulsifier agent, as well as at least one cosmetic fat or oil, the "wt %" indications referring in each case to the total weight of the agent according to the present invention.

In a further preferred embodiment the agents according to the present invention are characterized in that they include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 20 to 65 wt %, preferably 25 to 60 wt %, particularly preferably 30 to 55 wt %, extraordinarily preferably 35 to 50 wt %, furthermore ethanol in a total quantity from 5 to 60 wt %, preferably 10 to 40 wt %, particularly preferably 15 to 35 wt %, extraordinarily preferably 20 to 30 wt %, as well as at least one hydrogel-forming substance in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably these agents according to the present invention are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In a further preferred embodiment the agents according to the present invention are characterized in that they are include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 15 to 90 wt %, preferably 25 to 60 wt %, particularly preferably 30 to 55 wt %, extraordinarily preferably 35 to 50 wt %, furthermore ethanol in a total quantity from 5 to 50 wt %, preferably 10 to 40 wt %, particularly preferably 15 to 35 wt %, extraordinarily preferably 20 to 30 wt %, as well as at least one hydrogel-forming substance in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably these agents according to the present invention as well are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In a further preferred embodiment the agents according to the present invention are characterized in that they are present as a water-in-oil emulsion and include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 15 to 90 wt %, preferably 25 to 60 wt %, particularly preferably 30 to 55 wt %, extraordinarily preferably 35 to 50 wt %, as well as at least one hydrogel-forming substance in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably these agents according to the present invention as well are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In another preferred embodiment the agents according to the present invention are characterized in that they are present as an oil-in water emulsion and include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 15 to 90 wt %, preferably 25 to 60 wt %, particularly preferably 30 to 55 wt %, extraordinarily preferably 35 to 50 wt %, furthermore ethanol in a total quantity from 5 to 50 wt %, preferably 10 to 40 wt %, particularly preferably 15 to 35 wt %, extraordinarily preferably 20 to 30 wt %, as well as at least one hydrogel-forming substance in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably these agents according to the present invention as well are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

Hydrogel-forming substances preferred according to the present invention are selected from cellulose ethers, principally hydroxyalkyl celluloses, in particular hydroxypropyl cellulose, hydroxypropylmethyl cellulose, hydroxyethyl cellulose, carboxymethyl cellulose, cetylhydroxyethyl cellulose, hydroxybutylmethyl cellulose, methylhydroxyethyl cellulose, furthermore xanthan gum, sclerotium gum, succinoglucans, polygalactomannans, in particular guar gums and locust bean gum, in particular guar gum and locust bean gum themselves and the nonionic hydroxyalkyl guar derivatives and locust bean gum derivatives, such as hydroxypropyl guar, carboxymethylhydroxypropyl guar, hydroxypropylmethyl guar, hydroxyethyl guar, and carboxymethyl guar, furthermore pectins, agar, carrageenan, tragacanth, gum arabic, karaya gum, tara gum, gellan, gelatin, casein, propylene glycol alginate, alginic acids and salts thereof, in particular sodium alginate, potassium alginate, and calcium alginate, furthermore polyvinylpyrrolidones, polyvinyl alcohols, polyacrylamides, furthermore (although less preferably) physically modified (e.g. by pregelatinization) and/or chemically modified starches, in particular hydroxypropylated starch phosphates and starch octenylsuccinates and aluminum, calcium, or sodium salts thereof, furthermore (again less preferably) acrylic acid-acrylate copolymers, acrylic acid-acrylamide copolymers, acrylic acid-vinylpyrrolidone copolymers, acrylic acid-vinyl-formamide copolymers, and polyacrylates. Particularly preferred hydrogel-forming agents are selected from cellulose ethers, principally from hydroxyalkyl celluloses, in particular from hydroxypropyl cellulose, hydroxypropylmethyl cellulose, hydroxyethyl cellulose, carboxymethyl cellulose, cetylhydroxyethyl cellulose, hydroxybutylmethyl cellulose, and methylhydroxyethyl cellulose, as well as mixtures thereof. Hydroxyethyl cellulose and aluminum starch octenylsuccinate are extraordinarily preferred hydrogel-forming substances.

In a further preferred embodiment the agents according to the present invention are characterized in that they include water in a total quantity from 15 to 90 wt %, preferably 25 to 70 wt %, particularly preferably 30 to 60 wt %, extraordinarily preferably 35 to 50 wt %, furthermore ethanol in a total quantity from 5 to 50 wt %, preferably 10 to 40 wt %, particularly preferably 15 to 35 wt %, extraordinarily preferably 20 to 30 wt %, as well as hydroxyethyl cellulose in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably, these agents according to the present invention are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In a further preferred embodiment the agents according to the present invention are characterized in that they include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 15 to 90 wt %, preferably 25 to 70 wt %, particularly preferably 30 to 60 wt %, extraordinarily preferably 35 to 50 wt %, as well as hydroxyethyl cellulose in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably, these agents according to the present invention as well are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In a further preferred embodiment the agents according to the present invention are characterized in that they are present as an oil-in-water emulsion and include methanesulfonic acid and/or at least one physiologically acceptable salt thereof in a total quantity from 0.05 to 5 wt %, preferably 0.1 to 3 wt %, particularly preferably 0.5 to 2.5 wt %, extraordinarily preferably 1 to 2 wt %, furthermore water in a total quantity from 15 to 90 wt %, preferably 25 to 60 wt %, particularly preferably 30 to 55 wt %, extraordinarily preferably 35 to 50 wt %, furthermore ethanol in a total quantity from 5 to 60 wt %, preferably 10 to 40 wt %, particularly preferably 15 to 35 wt %, extraordinarily preferably 20 to 30 wt %, as well as aluminum starch octenylsuccinate in a total quantity from 0.01 to 2 wt %, preferably 0.1 to 1 wt %, preferably 0.2 to 0.7 wt %, extraordinarily preferably 0.3 to 0.5 wt %, the "wt %" indications referring in each case to the total weight of the agent according to the present invention; particularly preferably, these agents according to the present invention as well are present as a roll-on composition that is preferably packaged in a roll-on ball applicator and particularly preferably has a dynamic viscosity in the range from 300 to 10,000 mPas, preferably 800 to 7500 mPas, particularly preferably 1000 to 5000 mPas, measured with a Brookfield viscosimeter, spindle RV 4, 20 $s^{-1}$, no Helipath, at 20° C. ambient temperature and 20° C. sample temperature.

In order to further assist the discoloration-inhibiting action of methanesulfonic acid and/or the at least one physiologically acceptable salt of methanesulfonic acid, it can be advantageous to add to the agents according to the present invention at least one chelating agent that is selected from ethylenediaminetetraacetic acid (EDTA) and salts thereof, and from nitrilotriacetic acid (NTA) and mixtures of said substances, in a total quantity from 0.01 to 2.0 wt %, preferably 0.02 to 1 wt %, particularly preferably 0.05 to 0.3 wt %.

Further agents preferred according to the present invention are therefore characterized in that additionally at least one chelating agent that is selected from ethylenediaminetetraacetic acid (EDTA) and salts thereof, and from nitrilotriacetic acid (NTA) and mixtures of said substances, is included in a total quantity from 0.01 to 0.5 wt %, preferably 0.02 to 0.3 wt %, particularly preferably 0.05 to 0.1 wt %, the "wt %" indications referring in each case to the total weight of the agent.

Further compositions preferred according to the present invention optionally include at least one deodorant active substance in a total quantity from 0.001 to 40 wt %, preferably 0.2 to 20 wt %, particularly preferably 0.5 to 15 wt %, extraordinarily preferably 1.5 to 5 wt %, the "wt %" indications referring in each case to the total weight of the composition.

Ethanol is not regarded a deodorant active substance according to the present invention, but instead, if present, merely as a constituent of the carrier.

In a preferred embodiment the agents according to the present invention include as a deodorizing active substance at least one silver salt that is preferably selected from silver sulfate, silver nitrate, silver citrate, silver dihydrogen citrate, silver lactate, silver acetate, silver malate, silver succinate, silver tartrate, silver mandelate, silver salicylate, silver gluconate, silver adipate, and silver galactarate, and from mixtures of said salts. Silver sulfate, silver citrate, silver dihydrogen citrate, and silver lactate, as well as mixtures of said salts, are extraordinarily preferred.

Further preferred compositions according to the present invention include at least one silver salt that is preferably selected from silver sulfate, silver nitrate, silver citrate, silver dihydrogen citrate, silver lactate, silver acetate, silver malate, silver succinate, silver tartrate, silver mandelate, silver salicylate, silver gluconate, silver adipate, and silver galactarate, and from mixtures of said salts, in quantities such that silver is included in a total quantity from 1 to 100 ppm, preferably 2 to 50 ppm, particularly preferably 5 to 20 ppm, extraordinarily preferably 7 to 10 ppm, based in each case on the weight of the composition. The correspondingly required quantity of silver salt(s) can be calculated based on the molar masses of silver (107.87 g/mol) and of the respective silver salts (silver lactate, for example, has a molar mass of 196.94 g/mol).

In a further preferred embodiment the agents according to the present invention include as a deodorizing active substance at least one aromatic alcohol of structure (AA-1)

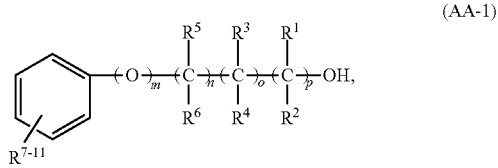

(AA-1)

where residues $R^1$ to $R^6$ mutually independently denote a hydrogen atom, an alkyl group having 1 to 10 carbon atoms, which can be linear or branched and can be substituted with OH groups or alkoxy groups having 1 to 5 carbon atoms, or an alkenyl group having 2 to. 10 carbon atoms, which can be linear or branched and can be substituted with OH groups or alkoxy groups having 1 to 5 carbon atoms, residues $R^7$ to $R^{11}$ mutually independently denote a hydrogen atom, a halogen atom, in particular a chlorine atom, or an alkyl group having 1 to 10 carbon atoms, which can be linear or branched and can be substituted with OH groups or alkoxy groups having 1 to 5 carbon atoms, in particular with a methoxy group, m=0 or 1, n, o, p mutually independently are integers from 0 to 10, at least one of the values n, o, p being not equal to 0.

Particularly preferred products according to the present invention include at least one alcohol AA-1 as described above which is selected from anise alcohol, 2-methyl-5-phenyl-pentan-1-ol, 1,1-dimethyl-3-phenylpropan-1-ol, benzyl alcohol, 2-phenylethan-1-ol, 3-phenylpropan-1-ol, 4-phenylbutan-1-ol, 5-phenylpentan-1-ol, 2 benzylheptan-1-ol, 2,2-dimethyl-3-phenylpropan-1-ol, 2,2 dimethyl-3-(3'-methylphenyl)propan-1-ol, 2-ethyl-3-phenylpropan-1-ol, 2-ethyl-3-(3'-methylphenyl)propan-1-ol, 3-(3'-chlorophenyl)-2-ethylpropan-1-ol, 3-(2'-chlorophenyl)-2-ethylpropan-1-ol, 3 (4'-chlorophenyl)-2-ethylpropan-1-ol, 3-(3',4'-dichlorophenyl)-2-ethylpropan-1-ol, 2-ethyl-3-(2'-methylphenyl)propan-1-ol, 2-ethyl-3-(4'-methylphenyl)propan-1-ol, 3-(3',4'-dimethylphenyl)-2-ethylpropan-1-ol, 2-ethyl-3-(4'-methoxyphenyl)propan-1-ol, 3-(3',4'-dimethoxyphenyl)-2-ethylpropan-1-ol, 2-allyl-3-phenylpropan-1-ol, and 2 n-pentyl-3-phenylpropan-1-ol, as well as mixtures thereof. 2 Benzylheptan-1-ol, as well as mixtures of 2 benzylheptan-1-ol and phenoxyethanol, are extraordinarily preferred. Further particular preferred compositions according to the present invention include at least one alcohol AA-1 as described above in a total quantity from 0.05 to 10 wt %, preferably 0.1 to 5 wt %, particularly preferably 0.2 to 2 wt %, extraordinarily preferably 0.3 to 1.5 wt %, based in each case on the weight of the composition. Extraordinarily preferred agents according to the present invention include 2-benzylheptan-1-ol in a total quantity from 0.05 to 1.5 wt %, preferably 0.1 to 1 wt %, particularly preferably 0.2 to 0.5 wt %, based in each case on the weight of the composition.

In a further preferred embodiment the agents according to the present invention include as a deodorant active substance at least one 1,2-alkanediol having 5 to 12 carbon atoms, which can be described by the formula HO—$CH_2$—CH(OH)—$(CH_2)_n$—$CH_3$ in which n denotes the number 2, 3, 4, 5, 6, 7, 8, or 9, as well as mixtures of said 1,2-alkanediols. 1,2-Alkanediols having 5 to 12 carbon atoms that are particularly preferred according to the present invention are selected from 1,2-pentanediol, 1,2-hexanediol, 1,2-octanediol, 1,2-decanediol, and mixtures thereof. A very particularly preferred combination according to the present invention is mixtures of 1,2-hexanediol and 1,2-octanediol, by preference at a weight ratio from 10:1 to 1:10, more preferably from 5:1 to 1:5, particularly preferably at a weight ratio of 1:1.

Preferred agents according to the present invention include at least one 1,2-alkanediol having 5 to 12 carbon atoms, which can be described by the formula HO—$CH_2$—CH(OH)—$(CH_2)_n$—$CH_3$ in which n denotes the number 2, 3, 4, 5, 6, 7, 8, or 9, in a total quantity from 0.2 to 15 wt %, preferably 0.3 to 10 wt %, particularly preferably 0.4 to 5 wt %, and extraordinarily preferably 0.5 to 2 wt %, based on each case on the weight of the composition. Extraordinarily preferred agents according to the present invention include 0.2 to 0.5 wt % 1,2-hexanediol and 0.2 to 0.5 wt % 1,2-octanediol, based in each case on the weight of the composition.

Further preferred agents according to the present invention are characterized by including the deodorant active substance 3-(2-ethylhexyloxy)-1,2-propanediol, preferably in a total quantity from 0.05 to 5 wt %, preferably 0.1 to 2 wt %, particularly preferably 0.2 to 1.5 wt %, extraordinarily preferably 0.5 to 1.0 wt %, based in each case on the weight of the composition.

Further preferred agents according to the present invention are characterized by including tropolone (2-hydroxy-2,4,6-cycloheptatrienone), preferably in a quantity from 0.001 to 0.1 wt %, based on the weight of the composition.

Further preferred agents according to the present invention are characterized by including the deodorant active substance triethyl citrate. Triethyl citrate is a known deodorant active substance that acts as an enzyme inhibitor for esterases and lipases and thus contributes to the broadband action of agents according to the present invention. Preferred agents according to the present invention include 0.5 to 15 wt %, preferably 3 to 8 wt %, extraordinarily preferably 4 to 6 wt %, based in each case on the weight of the composition.

Apocrine perspiration represents a complex mixture that includes, inter alia, sebum and other fats as well as steroids. Steroids themselves are not water-soluble. In order for them to be able to be transported away with the bodily fluids, they are normally present as a sulfate or glucuronide. On the skin, cleavage of these steroid esters into the volatile free steroids is accomplished by hydrolytic enzymes of skin bacteria, in particular of the coryneform bacteria. In principle, all bacterial exoesterases are capable of this, but in particular the enzymes arylsulfatase and beta-glucuronidase. Compounds that inhibit aryl sulfatase or beta-glucuronidase therefore represent deodorant active substances preferred according to the present invention.

Development of the short- and medium-chain fatty acids that contribute substantially to body odor begins with the cleavage of skin lipids to yield branched long-chain fatty acids. Cleavage of the skin lipids, which are present predominantly as glycerol esters, is accomplished substantially by Propionibacterium, Corynebacterium A, and Staphylococcus species (A. G. James et al., Generation and Turnover of Volatile Fatty Acids by Axillary Bacteria, $22^{nd}$ IFSCC Congress, Edinburgh, 2002, Poster 108). A. G. James et al. further disclose that both short-chain $C_2$ to $C_5$ fatty acids and medium-chain $C_6$ to $C_{12}$ fatty acids, which are principally responsible for axillary body odor, are formed from the long-chain branched fatty acids by the hydrolytic enzymes of a specific Corynebacterium that A. G. James et al. refer to as "Corynebacterium A." All bacterial exoesterases are in principle capable of this lipid cleavage, but in particular the enzyme lipase. Compounds that inhibit lipase therefore likewise represent deodorant active substances preferred according to the present invention.

A further class of compounds that likewise occurs in the context of bacterial breakdown of perspiration constituents and contributes to body odor is saturated and unsaturated aldehydes, chiefly those having a chain length from $C_6$ to $C_{12}$, in particular hexanal, heptanal, octenal, and nonenal. These are produced by beta-cleavage from the hydroperoxides that are formed by the action of 5-lipoxygenase on unsaturated fatty acids. Compounds that inhibit the enzyme 5-lipoxygenase therefore likewise represent deodorant active substances preferred according to the present invention.

It is furthermore known that highly foul-smelling components of human body odor and mouth odor represent volatile sulfur compounds (VSCs) that are released in particular by enzymatic reaction. Sulfur-including compounds occur as water-soluble amino acid conjugates with perspiration on human skin. There they are release by skin bacteria (chiefly Staphylococci and Corynebacteria) by enzymatic reaction. An enzyme that plays a particular role in the release of VSCs is cystathionine beta-lyase. This enzyme releases VSCs from the amino acids, and is thus an important cause of body odor. Compounds that inhibit the enzyme cystathionine beta-lyase therefore likewise represent deodorant active substances preferred according to the present invention.

Further preferred agents according to the present invention are characterized by including at least one compound that is an inhibitor of the enzyme arylsulfatase. Deodorant active substances preferred according to the present invention that act as an arylsulfatase inhibitor are those disclosed, for example, in U.S. Pat. Nos. 5,643,559, 5,676,937, WO 2001/099376 A2, EP 1430879 A1, and DE 10216368 A1. Further particularly preferred agents according to the present invention are characterized by including at least one compound that is an inhibitor of the enzyme arylsulfatase in a total quantity from 0.001 to 10 wt %, preferably 0.01 to 5 wt %, particularly preferably 0.1 to 2.5 wt %, based in each case on the weight of the composition.

Further preferred agents according to the present invention are characterized by including at least one compound that is an inhibitor of the enzyme beta-glucuronidase. Deodorant active substances preferred according to the present invention that act as beta-glucuronidase inhibitors are those disclosed, for example, in WO 2003/039505 A2. Further particularly preferred agents according to the present invention are characterized by including at least one compound that is an inhibitor of the enzyme beta-glucuronidase in a total quantity from 0.001 to 10 wt %, preferably 0.01 to 5 wt %, particularly preferably 0.1 to 2.5 wt %, based in each case on the weight of the composition.

Further agents preferred according to the present invention are characterized by including at least one compound that is an inhibitor of the enzyme lipase. Deodorant active substances preferred according to the present invention that act as lipase inhibitors are selected from those that are disclosed in EP 1428520 A2, furthermore selected from the aminomethylenemalonic acid derivatives according to DE 3018132 A1, the ethylene oxide-propylene oxide copolymers according to GB 2335596 A1, and the salts of phytic acid according to EP 650 720 A1. Further particularly preferred agents according to the present invention are characterized by including at least one compound that is an inhibitor of the enzyme lipase in a total quantity from 0.001 to 10 wt %, preferably 0.01 to 5 wt %, particularly preferably 0.1 to 2.5 wt %, based in each case on the weight of the composition.

Further particularly preferred agents according to the present invention are characterized by including at least one compound that is an inhibitor of 5-lipoxygenase. Deodorant active substances preferred according to the present invention that act as 5-lipoxygenase inhibitors are disclosed in EP 1428519 A2. Further particularly preferred agents according to the present invention are characterized by including at least one compound that is an inhibitor of the enzyme 5-lipoxygenase in a total quantity from 0.001 to 10 wt %, preferably 0.01 to 5 wt %, particularly preferably 0.1 to 2.5 wt %, based in each case on the weight of the composition.

Further particularly preferred agents according to the present invention are characterized by including at least one compound that is an inhibitor of the enzyme cystathionine beta-lyase. Deodorant active substances preferred according to the present invention that act as an inhibitor of cystathionine beta-lyase are selected from those disclosed in EP 495918 B1, WO 2006/079934, DE 102010000746 A1, WO 2010/031657 A1, and WO 2010/046291 A1. Further particular preferred agents according to the present invention are characterized by including at least one compound that is an inhibitor of the enzyme cystathionine beta-lyase in a total quantity from 0.001 to 10 wt %, preferably 0.01 to 5 wt %, particularly preferably 0.1 to 2.5 wt %, based in each case on the weight of the composition.

Further preferred agents according to the present invention are characterized by including at least one cationic phospholipid of formula KPL

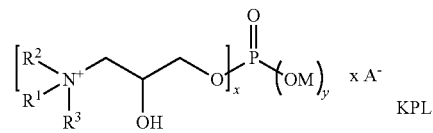

in which $R^1$ is an alkyl, alkenyl, or hydroxyalkyl group having 8 to 22 carbon atoms or an acylaminoalkyl group of the formula $R^5CONH(C_mH_{2m})$—, where $R^5CO$ is a linear acyl group having 8 to 22 carbon atoms and m=2 or 3, $R^2$ and $R^3$ are alkyl groups having 1 to 4 carbon atoms or hydroxyalkyl groups having 2 to 4 carbon atoms or carboxyalkyl groups of the formula $—(CH_2)_z—COOM$, in which z has a value from 1 to 3 and M is hydrogen or an alkali metal cation, x has a value from 1 to 3 and y a value of (3-x), M is hydrogen or an alkali metal cation, and $A^-$ is an anion.

Preferred alkyl groups having 8 to 22 carbon atoms are selected from an n-octyl, n-nonyl, n-decyl, n-undecyl, lauryl, n-tridecanyl, myristyl, n-pentadecanyl, cetyl, palmityl, stearyl, elaidyl, arachidyl, behenyl, and a cocyl group. A representative cocyl group is made up, based on its total weight, of 4 to 9 wt % n-octyl groups, 4 to 9 wt % n-decyl groups, 45 to 55 wt % lauryl groups, 15 to 21 wt % myristyl groups, 8 to 13 wt % palmityl groups, and 7 to 14 wt % stearyl groups. Preferred alkenyl groups having 8 to 22 carbon atoms are selected from a linoleyl group ((9Z,12Z)-octadeca-9,12-dien-1-yl) and a linolenyl group ((9Z,12Z,15Z)-octadeca-9,12,15-trien-1-yl). A preferred hydroxyalkyl group having 8 to 22 carbon atoms is selected from a 12-hydroxystearyl group.

Particularly preferred cationic phospholipids of formula KPL are those in which $R^1$ is an acylaminoalkyl group of the formula $R^5CONH(C_mH_{2m})$—, in which $R^5CO$ represents a linear acyl group having 8 to 22 carbon atoms and m=3.

Preferred linear acyl groups $R^5CO$ having 8 to 22 carbon atoms are selected from an n-octanoyl, n-nonanoyl, n-decanoyl, n-undecanoyl, lauroyl, n-tridecanoyl, myristoyl, n-pentadecanoyl, cetoyl, palmitoyl, stearoyl, elaidoyl, arachidoyl, behenoyl, and a cocoyl group. A representative cocoyl group is made up, based on its total weight, of 4 to 9 wt % n-octanoyl groups, 4 to 9 wt % n-decanoyl groups, 45 to 55 wt % lauroyl groups, 15-21 wt % myristoyl groups, 8 to 13 wt % palmitoyl groups, and 7 to 14 wt % stearoyl groups. Particularly preferred linear acyl groups $R^5CO$ are selected from a cocoyl group, a lauroyl group (n-$C_{11}H_{23}CO$), a myristoyl group (n-$C_{13}H_{27}CO$), and a linoleoyl group ((9Z,12Z)-octadeca-9,12-dien-1-oyl). Extraordinarily preferred linear acyl groups $R^5CO$ are selected from a cocoyl group, a lauroyl group (n-$C_{11}H_{23}CO$), and a myristoyl group (n-$C_{13}H_{27}CO$).

Preferred alkyl groups having 1 to 4 carbon atoms are a methyl, ethyl, n-propyl, 1-methylethyl, n-butyl, 2-methylpropyl, and tert-butyl group. The methyl group is particularly preferred.

Preferred hydroxyalkyl groups having 2 to 4 carbon atoms are a 2-hydroxyethyl group and a 1-hydroxyethyl group.

Preferred carboxyalkyl groups of the formula —$(CH_2)_z$—COOM, where z=1 to 3, are a carboxymethyl, a carboxyethyl, and a carboxy-n-propyl group.

Preferred alkali metal cations are selected from sodium and potassium cations; $Na^+$ is particularly preferred. Preferred anions are selected from sulfate, chloride, phosphate, nitrate, hydrogen carbonate, and acetate, a chloride anion being particularly preferred.

Preferred agents according to the present invention include as a deodorizing active substance a cationic phospholipid of formula KPL

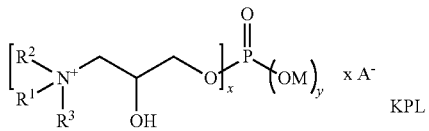

in which $R^1$ is an acylaminoalkyl group of the formula $R^5CONH(C_mH_{2m})$—, in which $R^5CO$ is selected from a cocoyl group, a lauroyl group, a myristoyl group, and a linoleoyl group, and m=3, $R^2$ and $R^3$ are methyl groups, x=2, y=1, M is a sodium ion, and $A^-$ is a chloride ion. Preferably at least one cationic phospholipid of formula KPL having the features recited above is included in a total quantity from 0.05 to 2 wt %, preferably 0.1 to 1 wt %, particularly preferably 0.15 to 0.4 wt %, based in each case on the weight of the agent.

Particularly preferred agents according to the present invention include a cationic phospholipid of formula KPL

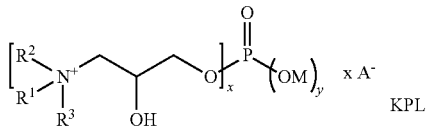

in which $R^1$ is a cocoylaminopropyl group (also referred to as a cocamidopropyl group), $R^2$ and $R^3$ are methyl groups, x=2, y=1, M is a sodium ion, and $A^-$ is a chloride ion, which is obtainable under the INCI name Cocoamidopropyl PG-Dimonium Chloride Phosphate, in a total quantity from 0.05 to 2 wt %, preferably 0.1 to 1 wt %, particularly preferably 0.15 to 0.4 wt %, based in each case on the weight of the agent.

Further particularly preferred agents according to the present invention include a cationic phospholipid of formula KPL

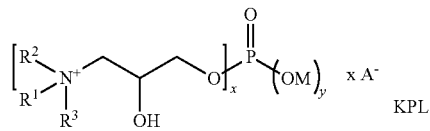

in which $R^1$ is a myristoylaminopropyl group, $R^2$ and $R^3$ are methyl groups, x=2, y=1, M is a sodium ion, and $A^-$ is a chloride ion, and which is obtainable under the INCI name Myristoamidopropyl PG-Dimonium Chloride Phosphate, in a total quantity from 0.05 to 2 wt %, preferably 0.1 to 1 wt %, particularly preferably 0.15 to 0.4 wt %, based in each case on the weight of the agent.

Further particularly preferred agents according to the present invention include a cationic phospholipid of formula KPL

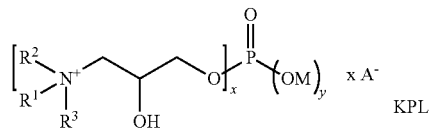

in which $R^1$ is a lauroylaminopropyl group, $R^2$ and $R^3$ are methyl groups, x=2, y=1, M is a sodium ion, and $A^-$ is a chloride ion, in a total quantity from 0.05 to 2 wt %, preferably 0.1 to 1 wt %, particularly preferably 0.15 to 0.4 wt %, based in each case on the weight of the agent.

Further deodorant active substances preferred according to the present invention are odor absorbers, ion exchangers having a deodorizing effect, germ-inhibiting agents, prebiotically effective components, and enzyme inhibitors, or (particularly preferably) combinations of the aforesaid active substances.

Silicates serve as odor absorbers which also, simultaneously, advantageously assist the rheological properties of the composition according to the present invention. Included among the silicates particularly preferred according to the present invention are chiefly sheet silicates, and among those in particular montmorillonite, kaolinite, illite, beidellite, nontronite, saponite, hectorite, bentonite, smectite, and talc. Further preferred odor absorbers are, for example, zeolites, zinc ricinoleate, cyclodextrins, specific metal oxides such as e.g. aluminum oxide, and chlorophyll. They are included preferably in a total quantity from 0.1 to 10 wt %, particularly preferably 0.5 to 7 wt %, and extraordinarily preferably 1 to 5 wt %, based in each case on the total composition.

"Germ-inhibiting" or "antimicrobial" active substances are understood according to the present invention as those active substances which reduce the number of skin microbes participating in odor formation, and/or inhibit their growth. Included among these microbes are, among others, various species from the group of Staphylococci, the group of Corynebacteria, Anaerococci, and Micrococci.

Germ-inhibiting or antimicrobial active substances preferred according to the present invention are in particular organohalogen compounds and organohalogen halides, quaternary ammonium compounds, a number of plant extracts, and zinc compounds. These include, among others, triclosan, chlorhexidine and chlorhexidine gluconate, 3,4,4'-trichlorocarbanilide, bromochlorophen, dichlorophen, chlorothymol, chloroxylenol, hexachlorophene, dichloro-m-xylenol, dequalinium chloride, domiphen bromide, ammonium phenolsulfonate, benzalkonium halides, benzalkonium cetyl phosphate, benzalkonium saccharinate, benzethonium chloride, cetylpyridinium chloride, laurylpyridinium chloride, laurylisoquinolinium bromide, methylbenzethonium chloride. In addition, phenol, phenoxyethanol, disodiumdihydroxyethylsulfosuccinyl undecylenate, sodium bicarbonate, zinc lactate, sodium phenolsulfonate and zinc phenolsulfonate, ketoglutaric acid, terpene alcohols such as e.g. farnesol, chlorophyllin-copper complexes, α-monoalkylglycerol ethers with a branched or linear, saturated or unsaturated, optionally hydroxylated $C_6$ to $C_{22}$ alkyl residue, particularly preferably α-(2-ethylhexyl) glycerol ether, available commercially as Sensiva® SC 50 (ex Schülke & Mayr), as well as carboxylic acid esters of mono-, di-, and triglycerol (e.g. glycerol monolaurate, diglycerol monocaprinate) are preferred deodorant active substances.

Preferred antiperspirant agents according to the present invention include at least one deodorant active substance that is selected from silver salts, aromatic alcohols of structure AA-1 having the substituents recited above, 1,2-alkanediols having 5 to 12 carbon atoms, alpha-(2-ethylhexyl)glycerol ether (3-2-ethylhexyloxy)-1,2-propanediol), tropolone, triethyl citrate, cationic phospholipids of formula KPL having the substituents recited above, as well as mixtures thereof.

Further preferred antiperspirant compositions according to the present invention are characterized in that the at least one deodorant active substance is included in a total quantity from 0.0001 to 20 wt %, preferably 1 to 15 wt %, particularly preferably 1.5 to 5 wt %, the "wt %" indications referring to the total weight of the composition.

Further preferred embodiments of the invention are characterized in that the cosmetic agent according to the present invention is present in stick form, liquid or gelled roll-on application, cream, lotion, solution, gel, or applied onto a substrate.

Preferred compositions according to the present invention that are present as an emulsion, suspension, stick, or gel preferably furthermore include at least one cosmetic oil that is liquid under standard conditions, that is not a fragrance and not an essential oil.

The cosmetic oil is liquid under standard conditions. "Essential oils" are understood according to the present invention as mixtures of volatile components that are produced by steam distillation from vegetable raw materials, e.g. citrus oils.

The total quantity, in compositions preferred according to the present invention, of cosmetic oils that are liquid under standard conditions and are not a fragrance and not an essential oil is 1 to 50 wt %, preferably 1.5 to 20 wt %, particularly preferably 2 to 10 wt %, extraordinarily preferably 3 to 6 wt %, the weight indications referring to the weight of the composition.

A distinction is made in the context of cosmetic oils between volatile and nonvolatile oils. "Nonvolatile" oils are understood as those oils that, at 20° C. and an ambient pressure of 1013 hPa, have a vapor pressure of less than 2.66 Pa (0.02 mm Hg). "Volatile" oils are understood as those oils that, at 20° C. and an ambient pressure of 1013 hPa, have a vapor pressure from 2.66 Pa to 40,000 Pa (0.02 mm to 300 mm Hg), preferably 10 to 12,000 Pa (0.1 to 90 mm Hg), particularly preferably 13 to 3000 Pa, extraordinarily preferably 15 to 500 Pa.

Volatile cosmetic oils are usually selected from among cyclic silicone oils having the INCI name Cyclomethicones. The INCI name Cyclomethicone is understood in particular to mean cyclotrisiloxane (hexamethylcyclotrisiloxane), cyclotetrasiloxane (octamethylcyclotetrasiloxane), cyclopentasiloxane (decamethylcyclopentasiloxane), and cyclohexasiloxane (dodecamethylcyclohexasiloxane). These oils have a vapor pressure of approx. 13 to 15 Pa at 20° C.

Cyclomethicones are known in the existing art as oils well suited for cosmetic compositions, in particular for deodorizing compositions such as sticks. Because of their persistence in the environment, however, it can be preferred according to the present invention to omit the use of cyclomethicones. In an especially preferred embodiment, the compositions according to the present invention and used according to the present invention include 0 to less than 1 wt %, preferably a maximum of 0.1 wt %, cyclomethicone, based on the weight of the composition.

A cyclomethicone replacement substance preferred according to the present invention is a mixture of $C_{13}$ to $C_{16}$ isoparaffins, $C_{12}$ to $C_{14}$ isoparaffins, and $C_{13}$ to $C_{15}$ alkanes whose viscosity at 25° C. is in the range from 2 to 6 mPas and which has a vapor pressure at 20° C. in the range from 10 to 150 Pa, preferably 100 to 150 Pa. A mixture of this kind is obtainable, for example, from Presperse Inc. under the name SiClone SR-5.

Further preferred silicone oils are selected from volatile linear silicone oils, in particular volatile linear silicone oils having 2 to 10 siloxane units, such as hexamethyldisiloxane ($L_2$), octamethyltrisiloxane ($L_3$), decamethyltetrasiloxane ($L_4$), as included e.g. in the commercial products DC 2-1184, Dow Corning® 200 (0.65 cSt), and Dow Corning® 200 (1.5 cSt) of Dow Corning, and low-molecular-weight Phenyl Trimethicone having a vapor pressure at 20° C. of approximately 2000 Pa, as obtainable e.g. from GE Bayer Silicones/Momentive under the name Baysilone Fluid PD 5.

Preferred antiperspirant compositions according to the present invention include, because of the drier skin feel and faster active-substance release, at least one volatile silicone oil, which can be cyclic or linear.

Further preferred compositions according to the present invention include, because of the drier skin feel and faster release of the antiperspirant active substance, at least one volatile non-silicone oil. Preferred volatile non-silicone oils are selected from $C_8$ to $C_{16}$ isoparaffins, in particular from isononane, isodecane, isoundecane, isododecane, isotridecane, isotetradecane, isopentadecane, and isohexadecane, as well as mixtures thereof. $C_{10}$ to $C_{13}$ isoparaffin mixtures, in particular those having a vapor pressure at 20° C. from 10 to 400 Pa, preferably 13 to 100 Pa, are preferred.

This at least one $C_8$ to $C_{16}$ isoparaffin is included preferably in a total quantity from 1 to 50 wt %, preferably 1.5 to 20 wt %, particularly preferably 2 to 10 wt %, extraordinarily preferably 3 to 6 wt %, based in each case on the total weight of the composition.

Further compositions preferred according to the present invention include at least one nonvolatile cosmetic oil selected from nonvolatile silicone oils and nonvolatile non-silicone oils. Residua of constituents insoluble in the composition, such as talc, but also the antiperspirant active substances (=perspiration-inhibiting aluminum salts) dried onto the skin, can be successfully masked with a nonvolatile oil. In addition, using a mixture of various oils, in particular of nonvolatile and volatile oil, parameters such as skin feel, visibility of residua, and stability of the composition according to the present invention can be precisely regulated and better adapted to consumers' needs.

Agents preferred according to the present invention are characterized in that the cosmetic oil that is not a fragrance and not an essential oil encompasses at least one volatile oil having a vapor pressure from 10 to 3000 Pa at 20° C. that is not a fragrance and not an essential oil, in a total quantity from 10 to 100 wt %, particularly preferably 30 to 80 wt %, based in each case on the total weight of the cosmetic oils.

It is of course likewise possible to formulate agents according to the present invention having a small proportion of volatile oils—i.e. having 0.5 to 15 wt % volatile oils, based on the total weight of the agent—or even having no volatile oils.

Oils particularly preferred according to the present invention are esters of linear or branched, saturated or unsaturated fatty alcohols having 2 to 30 carbon atoms with linear or branched, saturated or unsaturated fatty acids having 2 to 30 carbon atoms, which can be hydroxylated. Be it noted in this regard that some esters of linear or branched $C_1$ to $C_{22}$ alkanols or $C_{14}$ to $C_{22}$ alkenols, and some triesters of glycerol with linear or branched $C_2$ to $C_{22}$ carboxylic acids, which can be saturated or unsaturated, are solid under standard conditions, such as e.g. cetyl stearate or glycerol tristearate (=stearin). These esters that are solid under standard conditions do not represent cosmetic oils according to the present invention, since they do not meet the criterion of "liquid under standard conditions." The categorization as to whether such an ester is liquid or solid under standard conditions is a matter of the skilled artisan's general knowledge.

Esters of linear or branched saturated fatty alcohols having 2 to 5 carbon atoms with linear or branched, saturated or unsaturated fatty acids having 3 to 18 carbon atoms, which can be hydroxylated, are preferred. Preferred examples thereof are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Also preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oleate, oleyl oleate, oleyl erucate, erucyl oleate, $C_{12}$ to $C_{15}$ alkyl lactate, and di-$C_{12}$ to $C_{13}$ alkyl malate, as well as benzoic acid esters of linear or branched $C_{8-22}$ alkanols. Benzoic acid $C_{12}$ to $C_{15}$ alkyl esters are particularly preferred, obtainable e.g. as a commercial product Finsolv® TN ($C_{12}$ to $C_{15}$ alkyl benzoate), as well as benzoic acid isostearyl esters, obtainable e.g. as Finsolv® SB, 2-ethylhexyl benzoate, obtainable e.g. as Finsolv® EB, and benzoic acid 2-octyldodecyl esters, obtainable e.g. as Finsolv® BOD.

Further oil components preferred according to the present invention are selected from $C_5$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, e.g. $C_{12}$ to $C_{15}$ alkyl lactate, and on $C_{12/13}$ alkanols branched in the 2-position, can be obtained under the trade name Cosmacol® from Nordmann, Rassmann GmbH & Co., Hamburg, in particular the commercial products Cosmacol® ESI, Cosmacol® EMI, and Cosmacol® ETI.

The use of isopropyl esters of $C_{12}$ to $C_{18}$ carboxylic acids, in particular the use of isopropyl myristate, and particularly preferably mixtures of isopropyl myristate with $C_{10}$ to $C_{13}$ isoparaffin mixtures, the latter preferably having a vapor pressure from 10 to 400 Pa at 20° C., has proven particularly advantageous, for example in terms of active substance release.

Agents preferred according to the present invention include at least one ester of linear or branched, saturated or unsaturated fatty alcohols having 2 to 30 carbon atoms with linear or branched, saturated or unsaturated fatty acids having 2 to 30 carbon atoms, which can be hydroxylated, in a total quantity from 1 to 30 wt %, preferably 5 to 26 wt %, particularly preferably 9 to 24 wt %, extraordinarily preferably 12 to 17 wt %, based in each case on the weight of the total composition.

A further particularly preferred ester oil is triethyl citrate. Further products preferred according to the present invention include triethyl citrate and at least one $C_8$ to $C_{16}$ isoparaffin selected from isononane, isodecane, isoundecane, isododecane, isotridecane, isotetradecane, isopentadecane, and isohexadecane, as well as mixtures of said isoparaffins. Further products preferred according to the present invention include triethyl citrate and at least one $C_8$ to $C_{16}$ isoparaffin selected from isononane, isodecane, isoundecane, isododecane, isotridecane, as well as mixtures of said $C_8$ to $C_{16}$ isoparaffins. Further products preferred according to the present invention include triethyl citrate and a mixture of isodecane, isoundecane, isododecane, and isotridecane.

Further nonvolatile non-silicone oils preferred according to the present invention are selected from branched saturated or unsaturated fatty alcohols having 6 to 30 carbon atoms. These alcohols are often also referred to as "Guerbet alcohols," since they are obtainable via the Guerbet reaction. Preferred alcohol oils are 2-hexyldecanol, 2-octyldodecanol, and 2-ethyhexyl alcohol. Isostearyl alcohol is likewise preferred. Further preferred nonvolatile oils are selected from mixtures of Guerbet alcohols and Guerbet alcohol esters, e.g. 2-hexyldecanol and 2-hexyldecyl laurate.

The term "triglyceride" used below means "glycerol triester." Further nonvolatile oils preferred according to the present invention are selected from triglycerides of linear or branched, saturated or unsaturated, optionally hydroxylated $C_{8-30}$ fatty acids, provided they are liquid under standard conditions. The use of natural oils, e.g. soy oil, cottonseed oil, sunflower oil, palm oil, palm kernel oil, linseed oil, almond oil, castor oil, corn oil, rapeseed oil, olive oil, sesame oil, thistle oil, wheat germ oil, peach-kernel oil, and the liquid components of coconut oil and the like, can be particularly suitable. Synthetic triglyceride oils are particularly preferred, in particular Capric/Caprylic Triglycerides, e.g. the commercial products Myritol® 318 or Myritol® 331 (BASF/BASF) having unbranched fatty acid esters, as well as glyceryl triisostearin and glyceryl tri(2-ethylhexanoate) having branched fatty acid esters. Triglyceride oils of this kind preferably account for a proportion of less than 50 wt % of the total weight of all cosmetic oils in the composition according to the present invention. Particularly preferably, the total weight of triglyceride oils is 0.5 to 25 wt %, preferably 1 to 5 wt %, based in each case on the total composition.

Further nonvolatile non-silicone oils particularly preferred according to the present invention are selected from dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl)succinate.

Further nonvolatile non-silicone oils particularly preferred according to the present invention are selected from addition products of 1 to 5 propylene oxide units with mono- or polyvalent $C_{8-22}$ alkanols such as octanol, decanol, decanediol, lauryl alcohol, myristyl alcohol, and stearyl alcohol, e.g. PPG-2 Myristyl Ether and PPG-3 Myristyl Ether.

Further nonvolatile non-silicone oils particularly preferred according to the present invention are selected from addition products of at least 6 ethylene oxide and/or propylene oxide units with mono- or polyvalent $C_{3-22}$ alkanols such as glycerol, butanol, butanediol, myristyl alcohol, and stearyl alcohol, which can be esterified if desired, e.g. PPG-14 Butyl Ether, PPG-9 Butyl Ether, PPG-10 Butanediol, and PPG-15 Stearyl Ether.

Further nonvolatile non-silicone oils particularly preferred according to the present invention are selected from symmetrical, asymmetrical, or cyclic esters of carbonic acid with $C_6$ to $C_{20}$ alcohols, e.g. di-n-caprylyl carbonate (Cetiol® CC), or di-(2-ethylhexyl) carbonate (Tegosoft DEC). Esters of carbonic acid with $C_1$ to $C_5$ alcohols, however, e.g. glycerol carbonate or propylene carbonate, are not compounds suitable as a cosmetic oil.

Further oils that can be preferred according to the present invention are selected from esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols. The total weight of dimer fatty acid esters is particularly preferably 0.5 to 10 wt %, preferably 1 to 5 wt %, based in each case on the total composition.

Further cosmetic oils that are particularly preferred according to the present invention are selected from nonvolatile silicone oils. Nonvolatile silicone oils preferred according to the present invention are selected from linear polyalkylsiloxanes having a kinematic viscosity at 25° C. of at least 5 cSt to 2000 cSt, selected in particular from linear polydimethylsiloxanes having a kinematic viscosity at 25° C. from 5 cSt to 2000 cSt, preferably 10 to 350 cSt, particularly preferably 50 to 100 cSt, such as those obtainable e.g. under the commercial names Dow Corning® 200 or Xiameter PMX from Dow Corning or Xiameter. Further preferred nonvolatile silicone oils are Phenyl Trimethicone having a kinematic viscosity at 25° C. from 10 to 100 cSt, preferably from 15 to 30 cSt, and Cetyl Dimethicone.

Natural and synthetic hydrocarbons preferred according to the present invention are selected from paraffin oils, isohexadecane, isoeicosane, polyisobutenes, and polydecenes, which are obtainable e.g. under the name Emery® 3004, 3006, 3010 or under the name Nexbase® 2004G from Nestle, as well as 1,3-di-(2-ethylhexyl)cyclohexane.

The compositions according to the present invention and used according to the present invention optionally include further carrier substances, adjuvants, and active substances.

Antiperspirant sticks according to the present invention can be present in gelled form, on the basis of a W/O emulsion, on the basis of an O/W emulsion, on the basis of a water-oil multiple emulsion, on the basis of a nanoemulsion, and on the basis of a microemulsion, where the oil phase can include at least one silicone component or can be made up of at least one silicone component. Gel sticks can be formulated on the basis of fatty acid soaps, dibenzylidene sorbitol, N-acylamino acid amides, 12-hydroxystearic acid, polyamides, polyamide derivatives, polysaccharides such as xanthan, polyglucomannans, guar, konjac, celluloses or starches, polyacrylates, polyacrylate derivatives, and other gel-forming agents.

Roll-on applications and creams can be present as a water-in-oil emulsion, oil-in-water emulsion, silicone oil-in-water emulsion, water-in-oil microemulsion, oil-in-water microemulsion, silicone oil-in-water microemulsion, alcohol solution, in particular ethanol solution, hydroalcohol solution, in particular solutions having more than 50 wt % of a water-ethanol mixture, glycol solution, in particular as a solution in 1,2-propylene glycol, glycerol, dipropylene glycol, and liquid (under standard conditions) polyethylene glycols, hydroglycol solution, polyol solution, water-polyol solution, and as an aqueous gel. All the aforesaid compositions can be thickened, for example on the basis of fatty acid soaps, dibenzylidene sorbitol, N-acylamino acid amides, 12-hydroxystearic acid, polyacrylates of the carbomer and carbopol type, polyacrylamides, and polysaccharides, which can be chemically and/or physically modified. The agents can be transparent, translucent, or opaque.

Lipid or Wax Matrix

If the agents according to the present invention are present in the form of a stick, they preferably include a lipid matrix or wax matrix encompassing at least one lipid component or wax component having a melting point>50° C.

Natural vegetable waxes, for example, are preferred according to the present invention, for example candelilla wax, carnauba wax, Japan wax, sugar cane wax, ouricury wax, cork wax, sunflower wax, fruit waxes such as orange wax, lemon wax, grapefruit wax, and animal waxes, e.g. beeswax, shellac waxes, and spermaceti. It can be particularly preferred for purposes of the invention to use hydrogenated or hardened waxes. Also usable as a wax component are chemically modified waxes, in particular the hard waxes such as e.g. montan ester waxes, hydrogenated jojoba waxes, and sasol waxes. Included among the synthetic waxes that are likewise preferred according to the present invention are, for example, polyalkylene waxes and polyethylene glycol waxes, $C_{20}$ to $C_{40}$ dialkyl esters of dimer acids, $C_{30-50}$ alkyl beeswax, and alkyl and aryl esters of dimer fatty acids.

A particularly preferred wax component is selected from at least one ester of a saturated monovalent $C_{16}$ to $C_{60}$ alcohol and a saturated $C_8$ to $C_{36}$ monocarboxylic acid. Also included thereamong according to the present invention are lactides, the cyclic double esters of α-hydroxycarboxylic acids of the corresponding chain length. Esters of fatty acids and long-chain alcohols have proven particularly advantageous for the composition according to the present invention since they impart outstanding sensory properties to the antiperspirant composition, and excellent stability to the stick as a whole. The esters are made up of saturated branched or unbranched monocarboxylic acids and saturated branched or unbranched monovalent alcohols. Esters of aromatic carboxylic acids or hydroxycarboxylic acids (e.g. 12-hydroxystearic acid) and saturated branched or unbranched alcohols are also usable according to the present invention, provided the wax component has a melting point>50° C. It is particularly preferred to select the wax components from the group of esters of saturated branched or unbranched alkanecarboxylic acids having a chain length from 12 to 24 carbon atoms and saturated branched or unbranched alcohols having a chain length from 16 to 50 carbon atoms, which have a melting point>50° C. $C_{16-36}$ alkyl stearates and $C_{18-38}$ alkylhydroxystearoyl stearates, $C_{20-40}$ alkyl erucates, and cetearyl behenate, can be particularly advantageous. The wax or the wax components have a melting point>50° C., preferably >60° C. A particularly preferred embodiment of the invention includes as a wax component a $C_{20}$ to $C_{40}$ alkyl stearate. A further particularly preferred embodiment of the invention includes as a wax component cetearyl behenate, i.e. mixtures of cetyl behenate and stearyl behenate.

Further preferred lipid components or wax components having a melting point>50° C. are triglycerides of saturated and optionally hydroxylated $C_{12-30}$ fatty acids, such as hardened triglyceride fats (hydrogenated palm oil, hydrogenated coconut oil, hydrogenated castor oil), glyceryl tribehenate (Tribehenin), or glyceryl tri-12-hydroxystearate, furthermore synthetic full esters of fatty acids and glycols or polyols having 2 to 6 carbon atoms, provided they have a melting point above 50° C., for example preferably $C_{18}$-$C_{36}$ Acid Triglyceride (Syncrowax® HGL-C). Hydrogenated castor oil, obtainable e.g. as a commercial product Cutina® FIR, is particularly preferred according to the present invention as a wax component.

Further preferred lipid components or wax components having a melting point>50° C. are the saturated linear $C_{14}$ to $C_{36}$ carboxylic acids, in particular myristic acid, palmitic acid, stearic acid, and behenic acid, as well as mixtures of these compounds.

Preferred antiperspirant sticks according to the present invention include a lipid component or wax component that is selected from esters of a saturated monovalent $C_{16}$ to $C_{60}$ alkanol and a saturated $C_8$ to $C_{36}$ monocarboxylic acid, in particular cetyl behenate, stearyl behenate, and $C_{20}$ to $C_{40}$ alkyl stearate, glycerol triesters of saturated linear $C_{12}$ to $C_{30}$ carboxylic acids, which can be hydroxylated, candellila wax, carnauba wax, beeswax, saturated linear $C_{14}$ to $C_{36}$ carboxylic acids, as well as mixtures of the substances recited above. Particularly preferred mixtures of lipid components or wax components are selected from mixtures of cetyl behenate, stearyl behenate, hardened castor oil, palmitic acid, and stearic acid. Further particularly preferred mixtures of lipid or wax components are selected from mixtures of $C_{20}$ to $C_{40}$ alkyl stearate, hardened castor oil, palmitic acid, and stearic acid. Further preferred antiperspirant sticks according to the present invention include (a) lipid component(s) or (a) wax component(s) in total in a quantity from 0.5 to 30 wt %, preferably 1 to 25 wt %, based on the total composition.

Particularly preferably, the agents according to the present invention additionally include at least one emulsifier agent and/or at least one surfactant.

Suitable emulsifier agents and surfactants preferred according to the present invention are selected from anionic, cationic, nonionic, amphoteric, in particular ampholytic and zwitterionic, emulsifier agents and surfactants.

Surfactants are amphiphilic (bifunctional) compounds that are made up of at least one hydrophobic and at least one hydrophilic molecular part. The hydrophobic residue is preferably a hydrocarbon chain having 8 to 28 carbon atoms, which can be saturated or unsaturated, linear or branched. This $C_8$ to $C_{28}$ alkyl chain is particularly preferably linear.

The fundamental properties of surfactants and emulsifier agents are oriented absorption onto interfaces, as well as aggregation into micelles and formation of lyotrophic phases.

"Anionic surfactants" are understood as surfactants having exclusively anionic charges; they include, for example, carboxyl groups, sulfonic acid groups, or sulfate groups. Particularly preferred anionic surfactants are alkyl sulfates, alkyl ether sulfates, acyl glutamates, and C8 to C24 carboxylic acids, as well as salts thereof (called "soaps").

"Cationic surfactants" are understood as surfactants having exclusively cationic charges; they include, for example, quaternary ammonium groups. Cationic surfactants of the quaternary ammonium compound, esterquat, and amidoamine types are preferred. Preferred quaternary ammonium compounds are ammonium halides as well as the imidazolium compounds known by the INCI names Quaternium-27 and Quaternium-83. Further cationic surfactants usable according to the present invention are represented by quaternized protein hydrolysates. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Cationic surfactants are included in the agents preferred according to the present invention preferably in proportions from 0.05 to 10 wt %, based on the total agent.

Amphoteric surfactants are subdivided into ampholytic surfactants and zwitterionic surfactants. "Ampholytic" surfactants are understood as those surface-active compounds which possess both acidic (e.g. —COOH or $SO_3H$ groups) and basic hydrophilic groups (e.g. amino groups), and therefore behave in either acidic or basic fashion depending on conditions. One skilled in the art understands "zwitterionic" surfactants as surfactants that carry both a negative and a positive charge in the same molecule.

Examples of preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines, having in each case 8 to 24 carbon atoms in the alkyl group.

Examples of preferred ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case 8 to 24 carbon atoms in the alkyl group.

Oil-in-Water Emulsifier Agents

The compositions according to the present invention that are formulated as an emulsion, in particular as an oil-in-water emulsion, preferably include at least one nonionic oil-in-water emulsifier agent having an HLB value from more than 7 to 20. These are emulsifier agents commonly known to one skilled in the art, as listed e.g. in Kirk-Othmer, "Encyclopedia of Chemical Technology", 3rd ed., 1979, Vol. 8, pp. 913-916. For ethoxylated products, the HLB value is calculated using the formula HLB=(100−L): 5, where L is the weight proportion of the lipophilic groups, i.e. the fatty alkyl or fatty acyl groups, in the ethylene oxide adducts, expressed as percent by weight.

When selecting nonionic oil-in-water emulsifier agents suitable according to the present invention, it is particularly preferred to use a mixture of nonionic oil-in-water emulsifiers so that the stability of the stick compositions according to the present invention can be optimally adjusted. The individual emulsifier agent components provide in this context a portion of the overall HLB value or average HLB value of the oil-in-water emulsifier agent mixture in accordance with their quantitative proportion in terms of the total quantity of oil-in-water emulsifier agents. According to the present invention the average HLB value of the oil-in-water emulsifier agent mixture is equal to 10 to 19, preferably 12 to 18, and particularly preferably 14 to 17. In order to achieve such average HLB values, it is preferred to combine oil-in-water emulsifier agents from the HLB value ranges 10 to 14, 14 to 16, and optionally 16 to 19 with one another. The oil-in-water emulsifier agent mixtures can of course also include nonionic emulsifier agents having HLB values in the range from >7 to 10 and 19 to 20; such emulsifier agent mixtures can likewise be preferred according to the present invention. In another preferred embodiment, however, the antiperspirant compositions according to the present invention can also include only a single oil-in-water emulsifier agent having an HLB value in the range from 10 to 19.

Preferred antiperspirant agents according to the present invention include at least one nonionic oil-in-water emulsifier agent that is selected from ethoxylated $C_8$ to $C_{24}$ alkanols having an average of 10 to 100 mol ethylene oxide per mol, ethoxylated $C_8$ to $C_{24}$ carboxylic acids having an average of 10 to 100 mol ethylene oxide per mol, silicone copolyols having ethylene oxide units or having ethylene oxide and propylene oxide units, alkylmono- and -oligoglycosides having 8 to 22 carbon atoms in the alkyl residue and ethoxylated analogs thereof, ethoxylated sterols, partial esters of polyglycerols having 2 to 10 glycerol units and esterified with 1 to 4 saturated or unsaturated, linear or branched, optionally hydroxylated $C_8$ to $C_{30}$ fatty acids, provided they have an HLB value of more than 7, as well as mixtures of the substances recited above.

The ethoxylated $C_8$ to $C_{24}$ alkanols have the formula $R^1OH(CH_2CH_2O)_nH$, where $R^1$ denotes a linear or branched alkyl residue and/or alkenyl residue having 8 to 24 carbon atoms, and n denotes the average number of ethylene oxide units per molecule, for numbers from 10 to 100, preferably 10 to 30 mol ethylene oxide per 1 mol caprylyl alcohol, 2-ethylhexyl alcohol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, as well as industrial mixtures thereof. Adducts of 10 to 100 mol ethylene oxide with industrial fatty alcohols having 12 to 18 carbon atoms, for example coconut, palm, palm kernel, or tallow fatty alcohol, are also suitable.

The ethoxylated $C_8$ to $C_{24}$ carboxylic acids have the formula $R^1(OCH_2CH_2)_nOH$, where $R^1$ denotes a linear or branched, saturated or unsaturated acyl residue having 8 to 24 carbon atoms and n denotes the average number of ethylene oxide units per molecule, for numbers from 10 to 100, preferably 10 to 30 mol ethylene oxide per 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachidic acid, gadoleic acid, behenic acid, erucic acid, and brassidic acid, as well as industrial mixtures thereof. Adducts of 10 to 100 mol ethylene oxide with industrial fatty acids having 12 to 18 carbon atoms, for example coconut, palm, palm kernel, or tallow fatty acid, are also suitable. PEG-50 monostearate, PEG-100 monostearate, PEG-50 monooleate, PEG-100 monooleate, PEG-50 monolaurate, and PEG-100 monolaurate are particularly preferred.

It is particularly preferred to use $C_{12}$ to $C_{18}$ alkanols or $C_{12}$ to $C_{18}$ carboxylic acids each having 10 to 30 units ethylene oxide per molecule, as well as mixtures of said substances, in particular Ceteth-12, Ceteth-20, Ceteth-30, Steareth-12, Steareth-20, Steareth-30, Laureth-12, and Beheneth-20.

$C_8$ to $C_{22}$ alkylmono- and -oligoglycosides are also preferably used. $C_8$ to $C_{22}$ alkylmono- and -oligoglycosides represent known, commercially usual surfactants and emulsifier agents. They are manufactured in particular by reacting glucose or oligosaccharides with primary alcohols having 8 to 22 carbon atoms. With regard to the glycoside residue, both monoglycosides in which a cyclic sugar residue is bound glycosidically to the fatty alcohol, and oligomeric glycosides having a degree of oligomerization up to approximately 8, preferably 1 to 2, are suitable. The degree of oligomerization is a statistical average that is based on a homolog distribution that is usual for industrial products of this kind. Products that are obtainable under the name Plantacare® include a glucosidically bound $C_8$ to $C_{16}$ alkyl group on an oligoglucoside residue whose average degree of oligomerization is 1 to 2, in particular 1.1 to 1.4. Particularly preferred $C_8$ to $C_{22}$ alkyl mono- and -oligoglycosides are selected from octyl glucoside, decyl glucoside, lauryl glucoside, palmityl glucoside, isostearyl glucoside, stearyl glucoside, arachidyl glucoside, and behenyl glucoside, as well as mixtures thereof. The acyl glucamides derived from glucamine are also suitable as nonionic oil-in-water emulsifier agents.

Ethoxylated sterols, in particular ethoxylated soy sterols, also represent oil-in-water emulsifiers suitable according to the present invention. The degree of ethoxylation must be greater than 5, preferably less than 10, in order to exhibit an HLB value greater than 7 to 20. Suitable commercial products are, for example, PEG-10 Soy Sterol, PEG-16 Soy Sterol, and PEG-25 Soy Sterol.

It is further preferred to use partial esters of polyglycerols having 2 to 10 glycerol units and esterified with 1 to 4 saturated or unsaturated, linear or branched, optionally hydroxylated $C_8$ to $C_{30}$ fatty acid esters, provided they have an HLB value in the range from more than 7 to 20. Diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, and decaglycerol trihydroxystearate are particularly preferred.

Particularly preferred antiperspirant agents according to the present invention are characterized in that the nonionic oil-in-water emulsifier agent is included in a total quantity from 0.5 to 10 wt %, particularly preferably 1 to 4 wt %, and extraordinarily preferably 1.5 to 3 wt %, based on the total composition.

Water-in-Oil Emulsifier Agents

Compositions preferred according to the present invention that are formulated as an emulsion or stick preferably furthermore include at least one nonionic water-in-oil emulsifier agent having an HLB value greater than 1.0 and less than or equal to 7.0, selected from mono- and diesters of ethylene glycol and the mono-, di-, tri-, and tetraesters of pentaerythritol with linear saturated fatty acids having 12 to 30, in particular 14 to 22 carbon atoms, which can be hydroxylated, as well as mixtures thereof, as consistency agents and/or water binders. The mono- and diesters are preferred according to the present invention. $C_{12}$ to $C_{30}$ fatty acid residues preferred according to the present invention are selected from lauric acid, myristic acid, palmitic acid, stearic acid, arachidic acid, and behenic acid residues; the stearic acid residue is particularly preferred. Nonionic water-in-oil emulsifier agents particularly preferred according to the present invention having an HLB value greater than 1.0 and less than or equal to 7.0 are selected from pentaerythrityl monostearate, pentaerythrityl distearate, pentaerythrityl tristearate, pentaerythrityl tetrastearate, ethylene glycol monostearate, ethylene glycol distearate, and mixtures thereof. Water-in-oil emulsifier agents particularly preferred according to the present invention having an HLB value greater than 1.0 and less than or equal to 7.0 are obtainable, for example, as commercial products Cutina® PES (INCI: Pentaerythrityl Distearate), Cutina® AGS (INCI: Glycol Distearate), or Cutina® EGMS (INCI: Glycol Stearate). These commercial products already represent mixtures of mono- and diesters (tri- and tetraesters are also included in the pentaerythrityl esters).

It can be preferred according to the present invention to use only a single water-in-oil emulsifier agent. In another preferred embodiment the compositions according to the present invention include mixtures, in particular industrial mixtures, of at least two water-in-oil emulsifier agents. An "industrial mixture" is understood, for example, as a commercial product such as Cutina® PES.

Besides the aforesaid water-in-oil emulsifier agents based on ethylene glycol esters or pentaerythrityl esters, in a preferred embodiment at least one further nonionic water-in-oil emulsifier agent having an HLB value greater than 1.0 and less than or equal to 7.0 can also be included, the proportion of which in terms of the total weight of nonionic water-in-oil emulsifier agents having an HLB value greater than 1.0 and less than or equal to 7.0 should, however, not be greater than 80%. In a particularly preferred embodiment, the compositions according to the present invention include the at least one addition water-in-oil emulsifier agent having an HLB value greater than 1.0 and less than or equal to 7.0 at a weight proportion of only a maximum of 10%, respectively are free of additional water-in-oil emulsifiers. Some of these additional suitable emulsifier agents are listed, for example, in Kirk-Othmer, "Encyclopedia of Chemical Technology", 3rd ed., 1979, Vol. 8, p. 913. As already mentioned, the HLB value can also be calculated for ethoxylated adducts.

The following are preferably suitable as water-in-oil emulsifier agents:

linear saturated alkanols having 12 to 30 carbon atoms, in particular having 16 to 22 carbon atoms, in particular cetyl alcohol, stearyl alcohol, arachidyl alcohol, behenyl alcohol, and lanolin alcohol, or mixtures of these alcohols such as those obtainable upon industrial hydrogenation of vegetable and animal fatty acids;

esters and, in particular, partial esters of a polyol having 3 to 6 carbon atoms and linear saturated and unsaturated fatty acids having 12 to 30, in particular 14 to 22 carbon atoms, which can be hydroxylated. Such esters or partial esters are, for example, mono- and diesters of glycerol or the monoesters of propylene glycol with linear saturated and unsaturated $C_{12}$ to $C_{30}$ carboxylic acids, which can be hydroxylated, in particular those, with palmitic and stearic acid, sorbitan mono-, di-, or triesters of linear saturated and unsaturated $C_{12}$ to $C_{30}$ carboxylic acids, which can be hydroxylated, in particular those of myristic acid, palmitic acid, stearic acid, or of mixtures of said fatty acids, and methylglucose mono- and diesters of linear saturated and unsaturated $C_{12}$ to $C_{30}$ carboxylic acids, which can be hydroxylated;

sterols, i.e. steroids that carry a hydroxyl group on the C3 atom of the steroid skeleton and are isolated both from animal tissue (zoosterols, e.g. cholesterol, lanosterol) and from plants (phytosterols, e.g. ergosterol, stigmasterol, sitosterol) and from fungi and yeasts (mycosterols), and can have a low degree of ethoxylation (1 to 5 EO);

alkanols and carboxylic acids each having 8 to 24 carbon atoms, in particular having 16 to 22 carbon atoms, in the alkyl group and 1 to 4 ethylene oxide units per molecule, which have an HLB value greater than 1.0 and less than or equal to 7.0;

glycerol monoethers of saturated and/or unsaturated, branched and/or unbranched alcohols having a chain length from 8 to 30, in particular 12 to 18 carbon atoms, partial esters of polyglycerols having n=2 to 10 glycerol units and esterified with 1 to 5 saturated or unsaturated, linear or branched, optionally hydroxylated $C_8$ to $C_{30}$ fatty acid esters, provided they have an HLB value less than or equal to 7;

as well as mixtures of the aforesaid substances.

It can be preferred according to the present invention to use only a single additional water-in-oil emulsifier agent. In another preferred embodiment, the compositions according to the present invention include mixtures, in particular industrial mixtures, of at least two additional water-in-oil emulsifier agents. An "industrial mixture" is understood, for example, as a commercial product such as Cutina® GMS, which represents a mixture of glyceryl monostearate and glyceryl distearate.

Additional water-in-oil emulsifier agents usable particularly advantageously are stearyl alcohol, cetyl alcohol, glyceryl monostearate, in particular in the form of the commercial products Cutina® GMS and Cutina® MD (ex BASF), glyceryl distearate, glyceryl monocaprinate, glyceryl monocaprylate, glyceryl monolaurate, glyceryl monomyristate, glyceryl monopalmitate, glyceryl monohydroxystearate, glyceryl monooleate, glyceryl monolanolate, glyceryl dimyristate, glyceryl dipalmitate, glyceryl dioleate, propylene glycol monostearate, propylene glycol monolaurate, sorbitan monocaprylate, sorbitan monolaurate, sorbitan monomyristate, sorbitan monopalmitate, sorbitan monostearate, sorbitan sesquistearate, sorbitan distearate, sorbitan dioleate, sorbitan sesquioleate, sucrose distearate, arachidyl alcohol, behenyl alcohol, polyethylene glycol (2)-stearyl ether (Steareth-2), Steareth-5, Oleth-2, diglycerol monostearate, diglycerol monoisostearate, diglycerol monooleate, diglycerol dihydroxystearate, diglycerol distearate, diglycerol dioleate, triglycerol distearate, tetraglycerol monostearate, tetraglycerol distearate, tetraglycerol tristearate, decaglycerol pentastearate, decaglycerol pentahydroxystearate, decaglycerol pentaisostearate, decaglycerol pentaoleate, Soy Sterol, PEG-1 Soy Sterol, PEG-5 Soy Sterol, PEG-2 Monolaurate, and PEG-2 Monostearate.

Particularly preferred antiperspirant compositions according to the present invention are characterized in that at least one water-in-oil emulsifier agent is included in a total quantity from 0.1 to 15 wt %, preferably 0.5 to 8.0 wt %, and particularly preferably 1 to 4 wt %, based on the total composition. Quantities from 2 to 3 wt %, based on the total weight of the composition, can furthermore be extraordinarily preferred according to the present invention.

The HLB values can be calculated according to Griffin, as presented or tabulated, for example, in the RÖMPP Chemie Lexikon [Chemical Lexicon], in particular in the online version of November 2003, and in the handbooks of Fiedler, Kirk-Othmer, and Janistyn (H. Janistyn, Handbuch der Kosmetika and Riechstoffe [Manual of cosmetics and fragrances], Hüthig-Verlag Heidelberg, 3rd ed. 1978, Vol. 1, p. 470 and Vol. 3, p. 68-78) cited therein under the keyword "HLB system." If there are different indications in the literature regarding the HLB value of a substance, that HLB value which is closest to the value calculated according to Griffin should be used for the teaching according to the present invention. If an unequivocal HLB value cannot be ascertained in this manner, the HLB value indicated by the manufacturer of the emulsifier agent is to be used for the teaching according to the present invention. If this is also not possible, the HLB value is to be ascertained experimentally.

Further preferred compositions according to the present invention are characterized in that the total content of nonionic and ionic emulsifier agents and/or surfactants having an HLB value above 8 is at most 20 wt %, preferably at most 15 wt %, particularly preferably at most 10 wt %, particularly preferably at most 7 wt %, further particularly preferably at most 4 wt %, and extraordinarily preferably at most 3 wt %, based in each case on the total composition according to the present invention.

Compositions particularly preferred according to the present invention that are formulated as a water-in-oil emulsion preferably furthermore include at least one water-in-oil emulsifier agent. The at least one water-in-oil emulsifier agent is included preferably in a quantity from 0.5 to 10 wt %, particularly preferably 1.0 to 1.5 to 2.5 wt %, based in each case on the total weight of the emulsion.

A group of water-in-oil emulsifier agents particularly preferred according to the present invention is the poly-($C_2$ to $C_3$) alkylene glycol-modified silicones whose previous INCI name was Dimethicone Copolyol, having the current INCI names PEG-x Dimethicone (where x=2 to 20, preferably 3 to 17, particularly preferably 11 to 12), Bis-PEG-y Dimethicone (where y=3 to 25, preferably 4 to 20), PEG/PPG a/b Dimethicone (where a and b mutually independently denote numbers from 2 to 30, preferably 3 to 30, and particularly preferably 12 to 20, in particular 14 to 18), Bis-PEG/PPG-c/d Dimethicone (where c and d mutually independently denote numbers from 10 to 25, preferably 14 to 20, and particularly preferably 14 to 16), and Bis-PEG/PPG-e/f PEG/PPG g/h Dimethicone (where e, f, g, and h mutually independently denote numbers from 10 to 20, preferably 14 to 18, and particularly preferably 16). PEG/PPG-18/18 Dimethicone, which is obtainable commercially in a 1:9 or 2.5:75 mixture with Cyclomethicone or Dimethicone as DC 3225 C or DC 5225 C, DC 5227-C, PEG/PPG-4/12 Dimethicone, which is obtainable under the designation Abil B 8852, and Bis-PEG/PPG-14/14 Dimethicone, which is obtainable commercially in a mixture with Cyclomethicone as Abil EM 97 (Goldschmidt), Bis-PEG/PPG-20/20 Dimethicone, which is obtainable under the designation Abil B 8832, PEG/PPG-5/3 Trisiloxane (Silsoft 305), and PEG/PPG-20/23 Dimethicone (Silsoft 430 and Silsoft 440), are particularly preferred.

Further W/O emulsifier agents preferred according to the present invention are poly-($C_2$ to $C_3$) alkylene glycol-modified silicones that are hydrophobically modified with $C_4$ to $C_{18}$ alkyl groups, particularly preferably Cetyl PEG/PPG-10/1 Dimethicone (formerly: Cetyl Dimethicone Copolyol, obtainable as Abil EM 90 or in a mixture of polyglyceryl-4 isostearate, Cetyl PEG/PPG-10/1 Dimethicone, and hexyl laurate under the commercial designation Abil WE 09), also Alkyl Methicone Copolyols.

Compositions particularly preferred according to the present invention furthermore include preferably at least one skin-cooling active substance. Skin-cooling active substances suitable according to the present invention are, for example, menthol, isopulegol, and menthol derivatives, e.g. menthyl lactate, menthyl glycolate, Menthyl Ethyl Oxamate, menthylpyrrolidonecarboxylic acid, menthyl methyl ether, menthoxypropanediol, menthone glycerol acetal (9-methyl-6-(1-methylethyl)-1,4-dioxaspiro (4.5)decane-2-methanol), monomenthyl succinate, and 2-hydroxymethyl-3,5,5-trimethylcyclohexanol. Menthol, isopulegol, menthyl lactate, menthoxypropanediol, and menthylpyrrolidonecarboxylic acid are preferred as skin-cooling active substances, as well as mixtures of these substances, in particular mixtures of menthol and menthyl lactate, menthol, menthol glycolate and menthyl lactate, menthol and menthoxypropanediol, or menthol and isopulegol.

It is particularly preferred according to the present invention that at least one skin-cooling active substance be included, in a total quantity from 0.01 to 2 wt %, particularly preferably 0.02 to 0.5 wt %, and extraordinarily preferably 0.05 to 0.2 wt %, based in each case on the total weight of the composition.

Preferred compositions according to the present invention furthermore include at least one water-soluble polyvalent $C_2$ to $C_9$ alkanol having 2 to 6 hydroxyl groups and/or at least one water-soluble polyethylene glycol having 3 to 20 ethylene oxide units, as well as mixtures thereof. These components are preferably selected from 1,2-propylene glycol, 2-methyl-1,3-propanediol, glycerol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, as well as mixtures of the aforesaid substances. Suitable water-soluble polyethylene glycols are selected from PEG-3, PEG-4, PEG-6, PEG-7, PEG-8, PEG-9, PEG-10, PEG-12, PEG-14, PEG-16, PEG-18, and PEG-20 as well as mixtures thereof; PEG-3 to PEG-8 are preferred.

Preferred antiperspirant agents according to the present invention include at least one water-soluble polyvalent $C_2$ to $C_9$ alkanol having 2 to 6 hydroxyl groups and/or at least one water-soluble polyethylene glycol having 3 to 20 ethylene oxide units, which is selected from 1,2-propylene glycol, 2-methyl-1,3-propanediol, glycerol, 1,2-butylene glycol, 1,3-butylene glycol, 1,4-butylene glycol, pentylene glycols such as 1,2-pentane diol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, as well as mixtures of the aforesaid substances.

Particularly preferred antiperspirant agents according to the present invention include at least one water-soluble polyvalent $C_2$ to $C_9$ alkanol having 2 to 6 hydroxyl groups and/or at least one water-soluble polyethylene glycol having 3 to 20 ethylene oxide units, in a total quantity from 3 to 30 wt %, preferably 8 to 25 wt %, particularly preferably 10 to 18 wt %, based in each case on the total weight of the agent.

Particularly preferred antiperspirant agents according to the present invention are characterized in that at least one lipid component or wax component having a melting point in the range from 25 to <50° C., selected from coconut fatty acid glycerol mono-, di-, and triesters, Butyrospermum Parkii (Shea Butter), and esters of saturated monovalent $C_8$ to $C_{18}$ alcohols with saturated $C_{12}$ to $C_{18}$ monocarboxylic acids, as well as mixtures of these substances, is included. These lower-melting-point lipid components or wax components allow the consistency of stick-form or cream-form products to be optimized, and visible residua on the skin to be minimized. Commercial products having the INCI name Cocoglycerides are particularly preferred, in particular the commercial products Novata® (ex BASF), particularly preferably Novata® AB, a mixture of $C_{12}$ to $C_{18}$ mono-, di-, and triglycerides that melts in the range from 30 to 32° C., as well as the products of the Softisan series (Sasol Germany GmbH) having the INCI name Hydrogenated Cocoglycerides, in particular Softisan 100, 133, 134, 138, 142. Further preferred esters of saturated monovalent $C_{12}$ to $C_{18}$ alcohols with saturated $C_{12}$ to $C_{18}$ monocarboxylic acids are stearyl laurate, cetearyl stearate (e.g. Crodamol® CSS), cetyl palmitate (e.g. Cutina® CP), and myristyl myristate (e.g. Cetiol® MM).

Further particularly preferred antiperspirant agents according to the present invention are characterized in that they include at least one lipid component or wax component having a melting point in the range from 25 to <50° C., in quantities from 0.01 to 20 wt %, preferably 3 to 20 wt %, particularly preferably 5 to 18 wt %, and extraordinarily preferably 6 to 15 wt %, based on the total composition.

Particularly preferred antiperspirant agents according to the present invention furthermore include, in order to consolidate the consistency and improve sensory properties, at least one solid, water-insoluble, particulate filler. In an extraordinarily preferred embodiment, this filler is selected from optionally modified starches (e.g. from corn, rice, potatoes) and starch derivatives, which if desired are pregelatinized, in particular starch derivatives of the DRY FLO® type, cellulose and cellulose derivatives, silicon dioxide, silicic acids, e.g. Aerosil® grades, spherical polyalkylsesquisiloxane particles (in particular Aerosil® R972 and Aerosil® 200V of Degussa), silica gels, talc, kaolin, clays, e.g. bentonites, magnesium aluminum silicates, boron nitride, lactoglobulin derivatives, e.g. sodium $C_{8-16}$ isoalkylsuccinyllactoglobulin sulfonate, obtainable from Brooks Industries as a commercial product Biopol® OE, glass powders, polymer powders, in particular made of polyolefins, polycarbonates, polyurethanes, polyamides, e.g. nylon, polyesters, polystyrenes, polyacrylates, (meth)acrylate copolymers or (meth)acrylate-vinylidene copolymers, which can be crosslinked, or silicones, as well as mixtures of these substances. Polymer powders based on a polymethacrylate copolymer are obtainable, for example, as a commercial product Polytrap® 6603 (Dow Corning). Other polymer powders, for example based on polyamides, are obtainable under the designation Orgasol® 1002 (polyamide-6) and Orgasol® 2002 (polyamide-12) from Elf Atochem. Further polymer powders that are suitable for the purpose of the present invention are, for example, polymethacrylates (Micropearl® M of SEPPIC or Plastic Powder A of NIKKOL), styrene/divinylbenzene copolymers (Plastic Powder FP of NIKKOL), polyethylene and polypropylene powders (AC-CUREL® EP 400 of AKZO), or also silicone polymers (Silicone Powder X2-1605 of Dow Corning).

Particularly preferred antiperspirant agents according to the present invention include at least one solid, water-insoluble, particulate filler in a total quantity from 0.01 to 30 wt %, preferably 5 to 20 wt %, particularly preferably 8 to 15 wt %, based in each case on the total composition.

Particularly preferred antiperspirant agents according to the present invention further include at least one fragrance. The definition of a "fragrance" for purposes of the present Application corresponds to the definition usual in the art, as may be gathered from the RÖMPP Chemie Lexikon [Chemical Lexicon] as of December 2007. According to the latter, a fragrance is a chemical compound having an odor and/or taste that excites the receptors of the hair cells of the olfactory system (adequate stimulus). The physical and chemical properties necessary for this are a low molar mass of at most 300 g/mol, a high vapor pressure, minimal water solubility and high lipid solubility, as well as weak polarity and the presence of at least one osmophoric group in the molecule. In order to distinguish volatile low-molecular-weight substances that are usually (and also for purposes of the present Application) viewed and utilized not as fragrances but instead principally as solvents, for example ethanol, propanol, isopropanol, and acetone, from fragrances according to the present invention, fragrances according to the present invention have a molar mass from 74 to 300 g/mol, include at least one osmophoric group in the molecule, and have an odor and/or taste, i.e. they excite the receptors of the hair cells of the olfactory system.

Perfumes, perfume oils, or perfume oil constituents can be used as fragrances. Perfume oils or scents can be, according to the present invention, individual fragrance compounds, e.g. synthetic products of the ester, ether, aldehyde, ketone, alcohol, and hydrocarbon types. Fragrance compounds of the ester type are, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate, and jasmecyclate. The ethers include, for example, benzyl ethyl ether and ambroxan; the aldehydes, for example, the linear alkanals having 8 to 18 carbon atoms, citral, citronellal, citronellyloxyacetaldehyde, cyclamenaldehyde, lilial, and bourgeonal; the ketones, for example, the ionones, α-isomethylionone and methyl cedryl ketone; the alcohols, anethol, citronellol, eugenol, geraniol, linalool, phenylethyl alcohol and terpineol; and the hydrocarbons include principally the terpenes such as limonene and pinene. Preferably, however, mixtures of different fragrances that together produce an attractive fragrance note are used.

Particularly preferred antiperspirant agents according to the present invention include at least one fragrance component in a total quantity from 0.00001 to 10 wt %, preferably 0.5 to 7 wt %, extraordinarily preferably 1 to 6 wt %, based in each case on the total weight of the agent.

A further subject of the present Application is a method for nontherapeutic cosmetic perspiration-inhibiting treatment of the body in which a perspiration-inhibiting cosmetic agent that includes, in a cosmetically acceptable carrier, at least one perspiration-inhibiting aluminum salt in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the composition, and in addition thereto methanesulfonic acid and/or at least one physiologically acceptable salt of methanesulfonic acid, preferably in a total quantity from 0.05 to 5 wt %, preferably 0.1 to 3 wt %, particularly preferably 0.5 to 2.5 wt %, extraordinarily preferably 1 to 2 wt %, is applied onto the skin, in particular on the skin of the armpits, where the "wt %" indications refer in each case to the total weight of the agent.

The statements made with regard to the agents according to the present invention apply mutatis mutandis with regard to preferred embodiments of the method according to the present invention.

A further subject of the present Application is a method for preventing and/or reducing textile discolorations and/or textile spots, where the method comprises the following method steps:

a) producing a perspiration-inhibiting cosmetic agent by mixing at least one perspiration-inhibiting aluminum salt, which is preferably zirconium-free, in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the agent, with a cosmetically acceptable carrier and with at least one methanesulfonic acid of the following formula (MS-1)

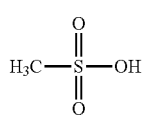
(MS-1)

or at least one physiologically acceptable salt of methanesulfonic acid, c) applying the perspiration-inhibiting cosmetic agent onto the skin, in particular onto the skin of the armpits,
d) wearing a textile garment over the treated skin, and
e) washing the textile garment, in particular repeatedly washing the textile garment, where no, or reduced, textile discolorations and/or textile spots occur after washing, in particular after repeated washing.

The statements made with regard to the agents according to the present invention apply mutatis mutandis with regard to preferred embodiments of the method according to the present invention for preventing and/or reducing textile discolorations.

EXPERIMENTAL SECTION

Anhydrous Antiperspirant Compositions

An oily suspension made up of 14.3 wt % activated aluminum chlorohydrate, 2 wt % of the methanesulfonic acid of formula (MS-1) used according to the present invention that is to be tested, as well as 73.1 wt % 2-ethylhexyl palmitate, 5.4% triethyl citrate, 3.9% Bentone 38 V CG, and 1.3% propylene carbonate, was produced as a test product according to the present invention (E-1). A suspension of this kind is, inter alia, representative of anhydrous antiperspirant roll-ons and anhydrous antiperspirant wax sticks.

A suspension made up of 14.3 wt % activated aluminum chlorohydrate and 67.9 wt % 2-ethylhexyl palmitate, 5.4% triethyl citrate, 3.9% Bentone 38 V CG, 1.3% propylene carbonate and 7.2 wt % perfume, was produced as a comparison product not according to the present invention (V 1).

TABLE 1

Test and comparison products used (quantities indicated in wt %)

| | V-1 | E-1 |
|---|---|---|
| Activated aluminum chlorohydrate (AACH) | 14.3 | 14.3 |
| 2-Ethylhexyl palmitate | 67.9 | 65.9 |
| Triethyl citrate | 5.4 | 5.4 |
| Benton 38 V CG | 3.9 | 3.9 |
| Propylene carbonate | 1.3 | 1.3 |
| Perfume | 7.2 | 7.2 |
| Methanesulfonic acid | — | 2 |

Experimental Procedure 0.3 gram of the respective test product or comparison product was applied directly onto a 10×10 cm² piece of light-blue cotton material (polo jersey, woven) that was stitched onto a waffle pique towel. After one hour of waiting time, 1 ml of an artificial perspiration mixture (MgCl$_2$, CaCl$_2$, KCl, NaCl, Na$_2$SO$_4$, NaH$_2$PO$_4$, glycine, glucose, lactic acid, urea; pH 5.2) was applied, and after a 24 hour waiting time (aging) the textile was washed in a standardized usual household washing process (Miele W 1714) and mechanically dried (Miele T 7644C).

TABLE 2

Further conditions of the washing tests

| | |
|---|---|
| Washing machine load | 3.5 kg |
| Water volume | 17 liters |
| Temperature | 40° C. |
| Main washing cycle time | 1 h |
| Pre-wash | none |
| Rinses | 4 x |
| Washing agent | Spee Color Gel, batch: HH06.1.1UWM1.08:58 |
| Washing agent portion weight | 75 ml (70 g) |
| Fabric softener | none |
| Dryer program | extra dry - cotton |

Product application and washing were repeated a total of eight times using the same textile (eight stain/wash cycles). Textile staining was evaluated visually by trained laboratory assistants on the basis of reference examples. The scale ranged from 0 (no stains) to 4 (very heavy staining). The evaluation was performed directly after completion of the washing series.

TABLE 3

Results of visual residuum evaluation

| | after 8th wash | | |
|---|---|---|---|
| Product | white | greasy | yellow |
| V-1 | 0 | 4 | 0 |
| E-1 | 0 | 2.5 | 0 |

The test product according to the present invention E-1, having 2 wt % methanesulfonic acid, exhibited an appreciably reduced formation of greasy stains on light-blue textile (Table 3) as compared with the comparison formulation V-1 having no methanesulfonic acid (Table 1).

Hydrous Antiperspirant Compositions

An aqueous solution made up of 20 wt % aluminum chlorohydrate, 2 wt % methanesulfonic acid, as well as 78 wt % water, was produced as a test product according to the present invention (E-2). A solution of this kind is representative, inter alia, of hydrous antiperspirant emulsions (antiperspirant roll-ons; antiperspirant sticks).

A solution made up of 20 wt % aluminum chlorohydrate and 80 wt % water was used as a comparison product not according to the present invention (V).

TABLE 4

Test and comparison products used (quantities indicated in wt %)

|  | V-2 | E-2 |
|---|---|---|
| Aluminum chlorohydrate (ACH) | 20 | 20 |
| Water | 80 | 78 |
| Methanesulfonic acid | — | 2 |

The washing tests were carried out analogously to the test series using the anhydrous compositions.

TABLE 5

Results of visual residuum evaluation

| | after 8th wash | | |
|---|---|---|---|
| Product | white | greasy | yellow |
| V-2 | 4 | 0 | 0 |
| E-2 | 2 | 0 | 0 |

The test product according to the present invention E-2, having 2 wt % methanesulfonic acid, exhibited an appreciably reduced formation of white spots on light-blue textile (Table 5) as compared with the comparison formulation V-2 having no methanesulfonic acid (Table 4).

Aqueous Antiperspirant Oil-in-Water Emulsion

An oil-in-water emulsion of the following composition E-3 was produced as a test product according to the present invention.

TABLE 6

Test emulsion (O/W) according and not according to the invention; quantities in wt %

|  | V-3 | E-3 |
|---|---|---|
| Aluminum chlorohydrate | 20.0 | 20.0 |
| Steareth-2 | 2.4 | 2.4 |
| Steareth-21 | 1.6 | 1.6 |
| Perfume | 1.2 | 1.2 |
| PPG-15 Stearyl Ether | 0.5 | 0.5 |
| Aluminum Starch Octenylsuccinate | 0.1 | 0.1 |
| Isopropyl myristate | 0.1 | 0.1 |
| Vitamin E acetate | 0.05 | 0.05 |
| EDTA powder | 0.095 | 0.095 |
| Methanesulfonic acid | — | 0.5 |
| Water | to 100.0 | to 100.0 |

A solution of this kind is representative of aqueous antiperspirant emulsions (antiperspirant roll-ons, antiperspirant sticks).

The washing tests were carried out similarly to the test series presented above, except that more washing cycles were carried out and the textiles were aged by being stored for 14 days. This allows the development of yellow stains to be simulated and evaluated.

Experimental Procedure 0.3 gram of the respective test product or comparison product was applied directly onto a 9.5×9.5 cm$^2$ piece of white cotton material (T-shirt material, knitted) that was stitched onto a waffle pique towel. After one hour of waiting time, 1 ml of an artificial perspiration mixture ($MgCl_2$, $CaCl_2$, KCl, NaCl, $Na_2SO_4$, $NaH_2PO_4$, glycine, glucose, lactic acid, urea; pH 5.2) was applied, and after a 24 hour waiting time (aging) the textile was washed in a standardized usual household washing process (Miele W 1714) and mechanically dried (Miele T 7644C). This stain/wash cycle was repeated a total of fourteen times.

TABLE 7

Further conditions of the washing tests

| | |
|---|---|
| Washing machine load | 3.5 kg |
| Water volume | 17 liters |
| Temperature | 40° C. |
| Main washing cycle time | 1 h |
| Pre-wash | none |
| Rinses | 4 x |
| Washing agent | Persil Gold universal powder with brightness formula Wero 2020110023 |
| Washing agent portion weight | 135 ml (80 g) |
| Fabric softener | none |
| Dryer program | extra dry - cotton |

Product application and washing were repeated a total of fourteen times using the same textile. Textile staining was evaluated visually by trained laboratory assistants on the basis of reference examples. The scale ranged from 0 (no stains) to 4 (very heavy staining). The evaluation was performed 14 days after completion of the washing series.

TABLE 8

Results of visual residuum evaluation

| | after 14 washes + 14 days aging | | |
|---|---|---|---|
| Product | white | greasy | yellow |
| V-3 | 0 | 0 | 2 |
| E-3 | 0 | 0 | 1 |

The test product according to the present invention E-3, having 0.5 wt % methanesulfonic acid, exhibited an appreciably reduced formation of white spots on white textile (Table 8) as compared with the comparison formulation V-3 having no methanesulfonic acid (Table 6).

In a further washing test using an anhydrous suspension based on a cyclopentasiloxane/isopropyl myristate oil mixture and 33 wt % activated aluminum chlorohydrate (as an example of an anhydrous roll-on suspension), an appreciable reduction in white spots on light-blue cotton material was seen with a 2-wt % methanesulfonic acid content.

Exemplifying Embodiments

The formulation examples that follow are intended to explain the subject matter of the invention without limiting it thereto.

1. Perspiration-inhibiting Suspension Sticks According to the Present Invention (Quantities Indicated in wt %)

| | 1.1 | 1.2 | 1.3 |
|---|---|---|---|
| Stearyl alcohol | 24.0 | 24.0 | 24.0 |
| Aluminum Zirconium Pentachlorohydrex Gly | 22.0 | 22.0 | 22.0 |
| PPG-14 Butyl Ether | 10.0 | 10.0 | 10.0 |

-continued

|  | 1.1 | 1.2 | 1.3 |
|---|---|---|---|
| Hardened castor oil (e.g. Cutina HR) | 3.0 | 3.0 | 3.0 |
| Myristyl myristate | 1.5 | 1.5 | 1.5 |
| DL-Menthol | 0.2 | 0.2 | 0.2 |
| Eucalyptol | 0.2 | 0.2 | 0.2 |
| Anethol | 0.2 | 0.2 | 0.2 |
| Silica Dimethyl Silylate | 1.4 | 1.4 | 1.4 |
| Silica | 0.3 | 0.3 | 0.3 |
| Methanesulfonic acid | 2.0 | 2.5 | 1.0 |
| Perfume | 2.0 | 2.0 | 2.0 |
| Cyclopentasiloxane | to 100 | to 100 | to 100 |

|  | 1.4 | 1.5 | 1.6 |
|---|---|---|---|
| Hydrogenated Castor Oil | 1.5 | 1.5 | 1.5 |
| Stearyl alcohol | 18 | 18 | 18 |
| Novata AB | 4 | 4 | 4 |
| PPG-14 Butyl Ether | 15.3 | 15.3 | 15.3 |
| Al—Zr Tetrahydrochlorex Gly (USP; number-average particle size: 3-20 µm) | 17.6 | 17.6 | 17.6 |
| Water of crystallization and (if present) glycine | 4.4 | 4.4 | 4.4 |
| Talc | 3 | 3 | 3 |
| Perfume | 1 | 1 | 1 |
| Eumulgin B1 | 3 | 3 | 3 |
| Methanesulfonic acid | 2.0 | 0.1 | 3.0 |
| Cyclomethicone (min. 95 wt % cyclopentasiloxane) | to 100 | to 100 | to 100 |

2. Antiperspirant Sticks According to the Present Invention in the Form of an Oil-in-Water Emulsion (Quantities Indicated in wt %)

|  | Example no. | |
|---|---|---|
|  | 2.1 | 2.2 |
| Cutina ® AGS | 2.5 | 2.5 |
| Cutina ® FS45 | 3.5 | 3.5 |
| Eumulgin ® B2 | 0.8 | 0.8 |
| Eumulgin ® B3 | 0.8 | 0.8 |
| Diisopropyl adipate | 6 | 6 |
| Novata ® AB | 4 | 4 |
| Cutina ® CP | 5 | 5 |
| Cutina ® HR | 4 | 4 |
| Kesterwachs K62 | 5 | 5 |
| Locron ® L (50% ACH solution) | 40 | 40 |
| Talc, Pharma G | 10 | 10 |
| Perfume | 1.2 | 1.2 |
| 2-Benzylheptan-1-ol | — | 0.3 |
| Sensiva SC 50 | 0.6 | 0.6 |
| Methanesulfonic acid | 2.0 | 3.0 |
| 1,2-Propanediol | 10 | 10 |
| Water, deionized | to 100.0 | to 100.0 |

Example 3: Antiperspirant Emulsion (O/W) According to the Present Invention (Indications in wt %)

| Ingredients | Wt % content |
|---|---|
| Aluminum Chlorohydrate | 20.0 |
| Steareth-2 | 2.4 |
| Steareth-21 | 1.6 |
| Perfume | 1.2 |
| PPG-15 Stearyl Ether | 0.5 |
| Aluminum Starch Octenylsuccinate | 0.1 |
| Methanesulfonic acid | 2.0 |
| Novata AB | 0.5 |
| Water | to 100.0 |

The emulsion according to Example 3 was decanted into a roll-on applicator.

4. Translucent Antiperspirant Microemulsions (Indications in wt %)

|  | 4.1 | 4.2 | 4.3 |
|---|---|---|---|
| Plantaren ® 1200 | 1.71 | 1.71 | — |
| Plantaren ® 2000 | 1.14 | 1.39 | 2.40 |
| Glycerol monooleate | 0.71 | 0.71 | — |
| Dioctyl ether | 4.00 | 4.00 | 0.09 |
| Octyl dodecanol | 1.00 | 1.00 | 0.02 |
| Perfume oil | 1.00 | 1.00 | 1.00 |
| Aluminum chlorohydrate | 8.00 | 5.00 | 5.00 |
| 1,2-Propylene glycol | 5.00 | 5.00 | — |
| Glycerol | — | — | 5.00 |
| 2-Benzylheptan-1-ol | 0.5 | — | — |
| Triethyl citrate | — | 0.5 | 0.5 |
| Triclosan | 0.1 | — | — |
| Methanesulfonic acid | 1.0 | 2.0 | 2.5 |
| Water | to 100 | to 100 | to 100 |

5. Antiperspirant Roll-ons (Indications in wt %)

|  | 5.1 | 5.2 |
|---|---|---|
| Ethanol, 96% (DEP denatured) | 30.0 | 30.0 |
| Mergital ® CS 11 | 2.0 | 2.0 |
| Eumulgin ® B3 | 2.0 | 2.0 |
| Aluminum chlorohydrate | 20.0 | 20.0 |
| Hydroxyethyl cellulose | 0.5 | 0.5 |
| Methanesulfonic acid | 2.5 | 0.5 |
| Cocamidopropyl PG-Dimonium Chloride Phosphate | 0.2 | — |
| Perfume oil | 0.8 | 0.8 |
| Water | to 100 | to 100 |

6. Antiperspirant Cloths (Examples 6.1 to 6.2)

For the embodiment according to the present invention as an antiperspirant cloth, a single-ply substrate made of 100% viscose having a basis weight of 50 g/m$^2$ was acted upon with 75 g per square meter of the respective example emulsions 5.1 or 5.2, or with 75 g of the respective example compositions 4.1 or 4.2, cut into cloths of suitable size, and packaged into sachets.

7. Antiperspirant Roll-on

|  | 7.1 | 7.2 |
|---|---|---|
| Aluminum chlorohydrate, 50% in water (Locron L) | 16.0 | 16.0 |
| Ethanol, 96% | 28.0 | 28.0 |
| Hydroxyethyl cellulose | 0.3 | 0.3 |
| Eumulgin B1 | 2.0 | 2.0 |
| Eumulgin B3 | 2.0 | 2.0 |
| Methanesulfonic acid | 2.5 | 1.5 |
| EDTA | — | 0.05 |
| Perfume | 1.0 | 1.0 |
| Water | to 100 | to 100 |

8. Antiperspirant Stick in the Form of a Water-in-Oil Emulsion

|  | 8.1 | 8.2 |
|---|---|---|
| Aluminum chlorohydrate, 50% in water | 35.6 | 35.6 |
| 1,2-Propylene glycol | 13.0 | 13.0 |
| Cyclohexasiloxane | 6.0 | 6.0 |
| Finsolv TN | 8.0 | 8.0 |
| Abil EM 90 | 1.2 | 1.2 |

-continued

|  | 8.1 | 8.2 |
|---|---|---|
| Polyethylene wax having molecular weight of 500 g/mol and a melting point in the range 83-91° C. | 10.0 | 10.0 |
| Polyalphaolefin wax having a molecular weight of 1800 g/mol and a melting point of 41° C. | 0.1 | 0.1 |
| Methanesulfonic acid | 2.0 | 0.5 |
| EDTA | — | 0.05 |
| Perfume | 1.0 | 1.0 |
| Water | to 100 | to 100 |

9. Clear Antiperspirant Gel

|  | 9.1 | 9.2 |
|---|---|---|
| Cyclopentasiloxane | 14.0 | 14.0 |
| Abil EM 97 | 3.0 | 3.0 |
| Ethanol, 96% | 10.0 | 10.0 |
| Aluminum chlorohydrate, 50% in water (Locron L) | 40.0 | 40.0 |
| 1,2-Propylene glycol | 20.3 | 20.3 |
| Water | 11.6 | 11.6 |
| Methanesulfonic acid | 2.0 | 0.5 |
| EDTA | — | 0.075 |
| Perfume | 1.0 | 1.0 |

List of Raw Materials Used

| Component | INCI | Supplier/Manufacturer |
|---|---|---|
| Abil EM 90 | Cetyl PEG/PPG-10/1 Dimethicone | Evonik |
| Abil EM 97 | Bis-PEG/PPG-14/14 Dimethicone, Cyclomethicone | Evonik |
| Cutina ® CP | Cetyl Palmitate | BASF |
| Cutina ® FS45 | Palmitic Acid, Stearic Acid | BASF |
| Cutina ® HR | Hydrogenated Castor Oil | BASF |
| Dow Corning ® 245 | Cyclopentasiloxane | Dow Corning |
| Dow Corning ES-5227 DM | Dimethicone, PEG/PPG-18/18 Dimethicone at 3:1 weight ratio | Dow Corning |
| Eumulgin ® B1 | Ceteareth-12 | BASF |
| Eumulgin ® B2 | Ceteareth-20 | BASF |
| Eumulgin ® B3 | Ceteareth-30 | BASF |
| Kesterwachs K62 | Cetearyl Behenate | Koster Keunen |
| Finsolv TN | C12-15 Alkyl Benzoate | Innospec |
| Locron L (50% ACH solution) | Aluminum Chlorohydrate | Clariant |
| Mergital ® CS 11 | Ceteareth-11 | BASF |
| Novata ® AB | Cocoglycerides (melting point 30-32° C.) | BASF |
| Plantaren ® 1200 | Lauryl Glucoside, approx. 50% AS | BASF |
| Plantaren ® 2000 | Decyl Glucoside, approx. 50% AS | BASF |
| Sensiva ® SC 50 | 2-ethylhexyl glycerol ether | Schülke & Mayr |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A perspiration-inhibiting cosmetic agent for nonaerosol utilization, comprising in a cosmetically acceptable carrier
   a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, where the "wt %" indications refer to the total weight of active substance (USP), free of water of crystallization and free of ligands, in the agent,
   and in addition thereto
   b) 0.05 to 5 wt %, based on the total weight of the agent, of a methanesulfonic acid of the following formula (MS-1)

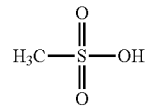

(MS-1)

or at least one physiologically acceptable salt of methanesulfonic acid selected from the group consisting of sodium, potassium, magnesium, calcium, manganese, zinc, and aluminum salts of methanesulfonic acid of formula (MS-1).

2. The agent according to claim 1, wherein at least one cosmetic oil that is not a fragrance and not an essential oil is included.

3. The agent according to claim 1, wherein zero to a maximum of 10 wt % free water is included, based on the total weight of the agent.

4. The agent according to claim 1, wherein free water is included in a total quantity from 15 to 96 wt % based on the total weight of the agent.

5. The agent according to claim 1, wherein at least one emulsifier agent and/or at least one surfactant is included.

6. The agent according to claim 1, wherein the agent is an oil-in-water emulsion.

7. The agent according to claim 1, wherein the agent is a water-in-oil emulsion.

8. The product according to claim 1, wherein the agent is an aqueous solution and furthermore includes ethanol.

9. The product according to claim 1, wherein the agent is a suspension of undissolved antiperspirant active substance in an oil.

10. The cosmetic agent according to claim 1, wherein the agent is formulated as a stick, soft solid, cream, roll-on, dibenzylidene alditol-based gel, loose powder, or compacted powder, or has been applied onto a disposable substrate being a cloth, pad, or wad.

11. The cosmetic agent according to claim 1, wherein no zirconium-including compounds are included.

12. A method for preventing and/or reducing textile discolorations and/or textile spots, where the method comprises the following method steps:
   a) producing a perspiration-inhibiting cosmetic agent by mixing at least one perspiration-inhibiting aluminum salt, which is preferably zirconium-free, in a total quantity from 2 to 40 wt %, preferably 8 to 35 wt %, particularly preferably 10 to 28 wt %, and extraordinarily preferably 12 to 20 wt %, where the "wt %"

indications refer to the total weight of active substance (USP), free of water of crystallization and free of ligands, in the agent, with a cosmetically acceptable carrier and with at least one methanesulfonic acid of the following formula (MS-1),

(MS-1)

or at least one physiologically acceptable salt of methanesulfonic acid,
b) applying the perspiration-inhibiting cosmetic agent onto the skin, in particular onto the skin of the armpits,
c) wearing a textile garment over the treated skin, and
d) washing the textile garment, in particular repeatedly washing the textile garment, where no, or reduced, textile discolorations and/or textile spots occur after washing, in particular after repeated washing.

\* \* \* \* \*